United States Patent
de Boer et al.

(10) Patent No.: US 7,630,083 B2
(45) Date of Patent: *Dec. 8, 2009

(54) APPARATUS AND METHOD FOR RANGING AND NOISE REDUCTION OF LOW COHERENCE INTERFEROMETRY LCI AND OPTICAL COHERENCE TOMOGRAPHY OCT SIGNALS BY PARALLEL DETECTION OF SPECTRAL BANDS

(75) Inventors: Johannes F. de Boer, Somerville, MA (US); Guillermo J. Tearney, Cambridge, MA (US); Brett Eugene Bouma, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/955,834

(22) Filed: Dec. 13, 2007

(65) Prior Publication Data

US 2008/0100837 A1 May 1, 2008

Related U.S. Application Data

(62) Division of application No. 10/501,276, filed as application No. PCT/US03/02349 on Jan. 24, 2003, now Pat. No. 7,355,716.

(60) Provisional application No. 60/351,904, filed on Jan. 24, 2002.

(51) Int. Cl.
*G01B 11/02* (2006.01)
*G01B 9/02* (2006.01)

(52) U.S. Cl. ........................... 356/479; 356/456

(58) Field of Classification Search .................. 356/456, 356/479, 497, 521, 451
See application file for complete search history.

(56) References Cited

U.S. PATENT DOCUMENTS 2,339,754 A    1/1944   Brace (Continued)

FOREIGN PATENT DOCUMENTS

DE    4309056    9/1994

(Continued)

OTHER PUBLICATIONS

Fujimoto et al., "High Resolution in Vivo Intra-Arterial Imaging with Optical Coherence Tomography," *Official Journal of the British Cardiac Society*, vol. 82, pp. 128-133 Heart, 1999.

(Continued)

*Primary Examiner*—Patrick J Connolly
(74) *Attorney, Agent, or Firm*—Dorsey & Whitney LLP

(57) ABSTRACT

Apparatus and method for increasing the sensitivity in the detection of optical coherence tomography and low coherence interferometry ("LCI") signals by detecting a parallel set of spectral bands, each band being a unique combination of optical frequencies. The LCI broad bandwidth source is split into N spectral bands. The N spectral bands are individually detected and processed to provide an increase in the signal-to-noise ratio by a factor of N. Each spectral band is detected by a separate photo detector and amplified. For each spectral band the signal is band pass filtered around the signal band by analog electronics and digitized, or, alternatively, the signal may be digitized and band pass filtered in software. As a consequence, the shot noise contribution to the signal is reduced by a factor equal to the number of spectral bands. The signal remains the same. The reduction of the shot noise increases the dynamic range and sensitivity of the system.

10 Claims, 19 Drawing Sheets

U.S. PATENT DOCUMENTS

| | | |
|---|---|---|
| 3,090,753 A | 5/1963 | Matuszak et al. |
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |
| 4,140,364 A | 2/1979 | Yamashita et al. |
| 4,141,362 A | 2/1979 | Wurster |
| 4,224,929 A | 9/1980 | Furihata |
| 4,295,738 A | 10/1981 | Meltz et al. |
| 4,300,816 A | 11/1981 | Snitzer et al. |
| 4,479,499 A | 10/1984 | Alfano |
| 4,533,247 A | 8/1985 | Epworth |
| 4,585,349 A | 4/1986 | Gross et al. |
| 4,601,036 A | 7/1986 | Faxvog et al. |
| 4,607,622 A | 8/1986 | Fritch et al. |
| 4,631,498 A | 12/1986 | Cutler |
| 4,650,327 A | 3/1987 | Ogi |
| 4,744,656 A | 5/1988 | Moran et al. |
| 4,751,706 A | 6/1988 | Rohde et al. |
| 4,770,492 A | 9/1988 | Levin et al. |
| 4,827,907 A | 5/1989 | Tashiro |
| 4,834,111 A | 5/1989 | Khanna et al. |
| 4,868,834 A | 9/1989 | Fox et al. |
| 4,890,901 A | 1/1990 | Cross, Jr. |
| 4,909,631 A | 3/1990 | Tan et al. |
| 4,925,302 A | 5/1990 | Cutler |
| 4,928,005 A | 5/1990 | Lefevre et al. |
| 4,965,441 A | 10/1990 | Picard |
| 4,993,834 A | 2/1991 | Carlhoff et al. |
| 4,998,972 A | 3/1991 | Chin et al. |
| 5,039,193 A | 8/1991 | Snow et al. |
| 5,040,889 A | 8/1991 | Keane |
| 5,045,936 A | 9/1991 | Lobb et al. |
| 5,046,501 A | 9/1991 | Crilly |
| 5,065,331 A | 11/1991 | Vachon et al. |
| 5,085,496 A | 2/1992 | Yoshida et al. |
| 5,120,953 A | 6/1992 | Harris |
| 5,121,983 A | 6/1992 | Lee |
| 5,127,730 A | 7/1992 | Brelje et al. |
| 5,197,470 A | 3/1993 | Helfer et al. |
| 5,202,745 A | 4/1993 | Sorin et al. |
| 5,212,667 A | 5/1993 | Tomlinson, Jr. et al. |
| 5,214,538 A | 5/1993 | Lobb |
| 5,241,364 A | 8/1993 | Kimura |
| 5,248,876 A | 9/1993 | Kerstens et al. |
| 5,250,186 A | 10/1993 | Dollinger et al. |
| 5,262,644 A | 11/1993 | Maguire |
| 5,291,885 A | 3/1994 | Taniji et al. |
| 5,293,872 A | 3/1994 | Alfano et al. |
| 5,293,873 A | 3/1994 | Fang |
| 5,304,173 A | 4/1994 | Kittrell et al. |
| 5,304,810 A | 4/1994 | Amos |
| 5,305,759 A | 4/1994 | Kaneko et al. |
| 5,317,389 A | 5/1994 | Hochberg et al. |
| 5,318,024 A | 6/1994 | Kittrell et al. |
| 5,321,501 A | 6/1994 | Swanson et al. |
| 5,348,003 A | 9/1994 | Caro |
| 5,353,790 A | 10/1994 | Jacques et al. |
| 5,383,467 A | 1/1995 | Auer et al. |
| 5,394,235 A | 2/1995 | Takeuchi et al. |
| 5,411,016 A | 5/1995 | Kume et al. |
| 5,419,323 A | 5/1995 | Kittrell et al. |
| 5,439,000 A | 8/1995 | Gunderson et al. |
| 5,441,053 A | 8/1995 | Lodder et al. |
| 5,450,203 A | 9/1995 | Penkethman |
| 5,454,807 A | 10/1995 | Lennox et al. |
| 5,459,325 A | 10/1995 | Hueton et al. |
| 5,459,570 A | 10/1995 | Swanson et al. |
| 5,465,147 A | 11/1995 | Swanson |
| 5,486,701 A | 1/1996 | Norton et al. |
| 5,491,524 A | 2/1996 | Hellmuth et al. |
| 5,491,552 A | 2/1996 | Knuttel |
| 5,526,338 A | 6/1996 | Hasman et al. |
| 5,555,087 A | 9/1996 | Miyagawa et al. |
| 5,562,100 A | 10/1996 | Kittrell et al. |
| 5,565,986 A * | 10/1996 | Knuttel ................ 356/456 |
| 5,566,267 A | 10/1996 | Neuberger |
| 5,583,342 A | 12/1996 | Ichie |
| 5,590,660 A | 1/1997 | MacAulay et al. |
| 5,600,486 A | 2/1997 | Gal et al. |
| 5,601,087 A | 2/1997 | Gunderson et al. |
| 5,621,830 A | 4/1997 | Lucey et al. |
| 5,623,336 A | 4/1997 | Raab et al. |
| 5,635,830 A | 6/1997 | Itoh |
| 5,649,924 A | 7/1997 | Everett et al. |
| 5,697,373 A | 12/1997 | Richards-Kortum et al. |
| 5,698,397 A | 12/1997 | Zarling et al. |
| 5,710,630 A | 1/1998 | Essenpreis et al. |
| 5,719,399 A | 2/1998 | Alfano et al. |
| 5,730,731 A | 3/1998 | Mollenauer et al. |
| 5,735,276 A | 4/1998 | Lemelson |
| 5,740,808 A | 4/1998 | Panescu et al. |
| 5,748,318 A | 5/1998 | Maris et al. |
| 5,748,598 A | 5/1998 | Swanson et al. |
| 5,784,352 A | 7/1998 | Swanson et al. |
| 5,785,651 A | 7/1998 | Kuhn et al. |
| 5,795,295 A | 8/1998 | Hellmuth et al. |
| 5,801,826 A | 9/1998 | Williams |
| 5,803,082 A | 9/1998 | Stapleton et al. |
| 5,807,261 A | 9/1998 | Benaron et al. |
| 5,817,144 A | 10/1998 | Gregory |
| 5,840,023 A | 11/1998 | Oraevsky et al. |
| 5,842,995 A | 12/1998 | Mahadevan-Jansen et al. |
| 5,843,000 A | 12/1998 | Nishioka et al. |
| 5,843,052 A | 12/1998 | Benja-Athon |
| 5,847,827 A | 12/1998 | Fercher |
| 5,862,273 A | 1/1999 | Pelletier |
| 5,865,754 A | 2/1999 | Sevick-Muraca et al. |
| 5,867,268 A | 2/1999 | Gelikonov et al. |
| 5,871,449 A | 2/1999 | Brown |
| 5,872,879 A | 2/1999 | Hamm |
| 5,877,856 A | 3/1999 | Fercher |
| 5,887,009 A | 3/1999 | Mandella et al. |
| 5,892,583 A | 4/1999 | Li |
| 5,910,839 A | 6/1999 | Erskine et al. |
| 5,912,764 A | 6/1999 | Togino |
| 5,920,373 A | 7/1999 | Bille |
| 5,920,390 A | 7/1999 | Farahi et al. |
| 5,921,926 A | 7/1999 | Rolland et al. |
| 5,926,592 A | 7/1999 | Harris et al. |
| 5,949,929 A | 9/1999 | Hamm |
| 5,951,482 A | 9/1999 | Winston et al. |
| 5,955,737 A | 9/1999 | Hallidy et al. |
| 5,956,355 A | 9/1999 | Swanson et al. |
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,010,449 A | 1/2000 | Selmon et al. |
| 6,014,214 A | 1/2000 | Li |
| 6,016,197 A * | 1/2000 | Krivoshlykov ............ 356/451 |
| 6,020,963 A | 2/2000 | Dimarzio et al. |
| 6,033,721 A | 3/2000 | Nassuphis |
| 6,044,288 A | 3/2000 | Wake et al. |
| 6,045,511 A | 4/2000 | Ott et al. |

| | | | |
|---|---|---|---|
| 6,048,742 A | 4/2000 | Weyburne et al. | |
| 6,053,613 A | 4/2000 | Wei et al. | |
| 6,069,698 A | 5/2000 | Ozawa et al. | |
| 6,091,496 A | 7/2000 | Hill | |
| 6,091,984 A | 7/2000 | Perelman et al. | |
| 6,111,645 A | 8/2000 | Tearney et al. | |
| 6,117,128 A | 9/2000 | Gregory | |
| 6,120,516 A | 9/2000 | Selmon et al. | |
| 6,134,003 A * | 10/2000 | Tearney et al. ............... 356/479 | |
| 6,134,010 A | 10/2000 | Zavislan | |
| 6,134,033 A | 10/2000 | Bergano et al. | |
| 6,141,577 A | 10/2000 | Rolland et al. | |
| 6,151,522 A | 11/2000 | Alfano et al. | |
| 6,159,445 A | 12/2000 | Klaveness et al. | |
| 6,160,826 A | 12/2000 | Swanson et al. | |
| 6,161,031 A | 12/2000 | Hochmann et al. | |
| 6,166,373 A | 12/2000 | Mao | |
| 6,174,291 B1 | 1/2001 | McMahon et al. | |
| 6,175,669 B1 | 1/2001 | Colston et al. | |
| 6,185,271 B1 | 2/2001 | Kinsinger | |
| 6,191,862 B1 | 2/2001 | Swanson et al. | |
| 6,193,676 B1 | 2/2001 | Winston et al. | |
| 6,198,956 B1 | 3/2001 | Dunne | |
| 6,201,989 B1 | 3/2001 | Whitehead et al. | |
| 6,208,415 B1 | 3/2001 | De Boer et al. | |
| 6,208,887 B1 | 3/2001 | Clarke | |
| 6,245,026 B1 | 6/2001 | Campbell et al. | |
| 6,249,349 B1 | 6/2001 | Lauer | |
| 6,249,381 B1 | 6/2001 | Suganuma | |
| 6,263,234 B1 | 7/2001 | Engelhardt et al. | |
| 6,264,610 B1 | 7/2001 | Zhu | |
| 6,272,376 B1 | 8/2001 | Marcu et al. | |
| 6,274,871 B1 | 8/2001 | Dukor et al. | |
| 6,282,011 B1 | 8/2001 | Tearney et al. | |
| 6,297,018 B1 | 10/2001 | French et al. | |
| 6,308,092 B1 | 10/2001 | Hoyns | |
| 6,324,419 B1 | 11/2001 | Guzelsu et al. | |
| 6,341,036 B1 | 1/2002 | Tearney et al. | |
| 6,353,693 B1 | 3/2002 | Kano et al. | |
| 6,374,128 B1 | 4/2002 | Toida et al. | |
| 6,377,349 B1 | 4/2002 | Fercher | |
| 6,384,915 B1 | 5/2002 | Everett et al. | |
| 6,393,312 B1 | 5/2002 | Hoyns | |
| 6,394,964 B1 | 5/2002 | Sievert, Jr. et al. | |
| 6,396,941 B1 | 5/2002 | Bacus et al. | |
| 6,421,164 B2 | 7/2002 | Tearney et al. | |
| 6,445,485 B1 | 9/2002 | Frigo et al. | |
| 6,445,944 B1 | 9/2002 | Ostrovsky | |
| 6,463,313 B1 | 10/2002 | Winston et al. | |
| 6,469,846 B2 | 10/2002 | Ebizuka et al. | |
| 6,475,159 B1 | 11/2002 | Casscells et al. | |
| 6,475,210 B1 | 11/2002 | Phelps et al. | |
| 6,477,403 B1 | 11/2002 | Eguchi et al. | |
| 6,485,413 B1 | 11/2002 | Boppart et al. | |
| 6,485,482 B1 | 11/2002 | Belef | |
| 6,501,551 B1 | 12/2002 | Tearney et al. | |
| 6,501,878 B2 | 12/2002 | Hughes et al. | |
| 6,538,817 B1 | 3/2003 | Farmer et al. | |
| 6,549,801 B1 | 4/2003 | Chen et al. | |
| 6,552,796 B2 | 4/2003 | Magnin et al. | |
| 6,556,305 B1 | 4/2003 | Aziz et al. | |
| 6,556,853 B1 | 4/2003 | Cabib et al. | |
| 6,558,324 B1 | 5/2003 | Von Behren et al. | |
| 6,564,087 B1 | 5/2003 | Pitris et al. | |
| 6,564,089 B2 | 5/2003 | Izatt et al. | |
| 6,567,585 B2 | 5/2003 | Harris | |
| 6,615,071 B1 | 9/2003 | Casscells, III et al. | |
| 6,622,732 B2 | 9/2003 | Constantz | |
| 6,680,780 B1 | 1/2004 | Fee | |
| 6,685,885 B2 | 2/2004 | Nolte et al. | |
| 6,687,007 B1 | 2/2004 | Meigs | |
| 6,687,010 B1 | 2/2004 | Horii et al. | |
| 6,701,181 B2 | 3/2004 | Tang et al. | |
| 6,738,144 B1 | 5/2004 | Dogariu | |
| 6,741,355 B2 | 5/2004 | Drabarek | |
| 6,757,467 B1 | 6/2004 | Rogers | |
| 6,790,175 B1 | 9/2004 | Furusawa et al. | |
| 6,806,963 B1 | 10/2004 | Wälti et al. | |
| 6,816,743 B2 | 11/2004 | Moreno et al. | |
| 6,839,496 B1 | 1/2005 | Mills et al. | |
| 6,909,105 B1 | 6/2005 | Heintzmann et al. | |
| 6,949,072 B2 | 9/2005 | Furnish et al. | |
| 6,980,299 B1 | 12/2005 | de Boer | |
| 7,006,231 B2 | 2/2006 | Ostrovsky et al. | |
| 7,019,838 B2 | 3/2006 | Izatt et al. | |
| 7,061,622 B2 | 6/2006 | Rollins et al. | |
| 7,190,464 B2 | 3/2007 | Alphonse | |
| 7,231,243 B2 | 6/2007 | Tearney et al. | |
| 7,236,637 B2 | 6/2007 | Sirohey et al. | |
| 7,242,480 B2 | 7/2007 | Alphonse | |
| 7,267,494 B2 | 9/2007 | Deng et al. | |
| 7,336,366 B2 | 2/2008 | Choma et al. | |
| 7,355,716 B2 | 4/2008 | De Boer et al. | |
| 7,359,062 B2 | 4/2008 | Chen et al. | |
| 7,366,376 B2 | 4/2008 | Shishkov et al. | |
| 7,391,520 B2 | 6/2008 | Zhou et al. | |
| 2001/0047137 A1 | 11/2001 | Moreno et al. | |
| 2002/0016533 A1 | 2/2002 | Marchitto et al. | |
| 2002/0048025 A1 | 4/2002 | Takaoka | |
| 2002/0048026 A1* | 4/2002 | Isshiki et al. ................ 356/498 | |
| 2002/0052547 A1 | 5/2002 | Toida | |
| 2002/0057431 A1 | 5/2002 | Fateley et al. | |
| 2002/0064341 A1 | 5/2002 | Fauver et al. | |
| 2002/0076152 A1 | 6/2002 | Hughes et al. | |
| 2002/0085209 A1 | 7/2002 | Mittleman et al. | |
| 2002/0091322 A1 | 7/2002 | Chaiken et al. | |
| 2002/0122246 A1 | 9/2002 | Tearney et al. | |
| 2002/0140942 A1 | 10/2002 | Fee et al. | |
| 2002/0158211 A1 | 10/2002 | Gillispie | |
| 2002/0161357 A1 | 10/2002 | Anderson et al. | |
| 2002/0163622 A1 | 11/2002 | Magnin et al. | |
| 2002/0168158 A1 | 11/2002 | Furusawa et al. | |
| 2002/0172485 A1 | 11/2002 | Keaton et al. | |
| 2002/0183623 A1 | 12/2002 | Tang et al. | |
| 2002/0188204 A1 | 12/2002 | McNamara et al. | |
| 2002/0196446 A1 | 12/2002 | Roth et al. | |
| 2002/0198457 A1 | 12/2002 | Tearney et al. | |
| 2003/0023153 A1 | 1/2003 | Izatt et al. | |
| 2003/0026735 A1 | 2/2003 | Nolte et al. | |
| 2003/0028114 A1 | 2/2003 | Casscells, III et al. | |
| 2003/0030816 A1 | 2/2003 | Eom et al. | |
| 2003/0082105 A1 | 5/2003 | Fischman et al. | |
| 2003/0097048 A1 | 5/2003 | Ryan et al. | |
| 2003/0108911 A1 | 6/2003 | Klimant et al. | |
| 2003/0120137 A1 | 6/2003 | Pawluczyk et al. | |
| 2003/0135101 A1 | 7/2003 | Webler | |
| 2003/0164952 A1 | 9/2003 | Deichmann et al. | |
| 2003/0171691 A1 | 9/2003 | Casscells, III et al. | |
| 2003/0174339 A1 | 9/2003 | Feldchtein et al. | |
| 2003/0220749 A1 | 11/2003 | Chen et al. | |
| 2003/0236443 A1 | 12/2003 | Cespedes et al. | |
| 2004/0002650 A1 | 1/2004 | Mandrusov et al. | |
| 2004/0054268 A1 | 3/2004 | Esenaliev et al. | |
| 2004/0072200 A1 | 4/2004 | Rigler et al. | |
| 2004/0077949 A1 | 4/2004 | Blofgett et al. | |
| 2004/0086245 A1 | 5/2004 | Farroni et al. | |
| 2004/0100631 A1 | 5/2004 | Bashkansky et al. | |
| 2004/0100681 A1 | 5/2004 | Bjarklev et al. | |
| 2004/0126048 A1 | 7/2004 | Dave et al. | |
| 2004/0150829 A1 | 8/2004 | Koch et al. | |
| 2004/0152989 A1 | 8/2004 | Puttappa et al. | |
| 2004/0166593 A1 | 8/2004 | Nolte et al. | |
| 2004/0239938 A1 | 12/2004 | Izatt | |
| 2004/0263843 A1 | 12/2004 | Knopp et al. | |
| 2005/0018201 A1 | 1/2005 | De Boer | |
| 2005/0035295 A1 | 2/2005 | Bouma et al. | |

| | | | |
|---|---|---|---|
| 2005/0046837 A1 | 3/2005 | Izumi et al. | |
| 2005/0057680 A1 | 3/2005 | Agan | |
| 2005/0057756 A1 | 3/2005 | Fang-Yen et al. | |
| 2005/0075547 A1 | 4/2005 | Wang | |
| 2005/0083534 A1 | 4/2005 | Riza et al. | |
| 2005/0165303 A1 | 7/2005 | Kleen et al. | |
| 2005/0171438 A1 | 8/2005 | Chen et al. | |
| 2006/0103850 A1 | 5/2006 | Alphonse et al. | |
| 2006/0146339 A1 | 7/2006 | Fujita et al. | |
| 2006/0244973 A1 | 11/2006 | Yun et al. | |
| 2007/0019208 A1 | 1/2007 | Toida et al. | |
| 2007/0070496 A1 | 3/2007 | Gweon et al. | |
| 2007/0291277 A1 | 12/2007 | Everett et al. | |

FOREIGN PATENT DOCUMENTS

| | | |
|---|---|---|
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 1324051 | 7/2003 |
| EP | 1426799 | 6/2004 |
| FR | 2738343 | 8/1995 |
| GB | 1257778 | 12/1971 |
| GB | 2030313 | 4/1980 |
| GB | 2209221 | 5/1989 |
| GB | 2298054 | 8/1996 |
| JP | 6073405 | 4/1985 |
| JP | 4135550 | 5/1992 |
| JP | 4135551 | 5/1992 |
| JP | 5509417 | 11/1993 |
| JP | 2002214127 | 7/2002 |
| WO | 7900841 | 10/1979 |
| WO | 9201966 | 2/1992 |
| WO | 9216865 | 10/1992 |
| WO | 9219930 | 11/1992 |
| WO | 9303672 | 3/1993 |
| WO | 9216865 | 10/1993 |
| WO | 9533971 | 12/1995 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 1998048846 | 11/1998 |
| WO | 9944089 | 9/1999 |
| WO | 9957507 | 11/1999 |
| WO | 0058766 | 10/2000 |
| WO | 0101111 | 1/2001 |
| WO | 2001027679 | 4/2001 |
| WO | 0138820 | 5/2001 |
| WO | 0142735 | 6/2001 |
| WO | 0236015 | 5/2002 |
| WO | 0238040 | 5/2002 |
| WO | 02054027 | 7/2002 |
| WO | 2002084263 | 10/2002 |
| WO | 03020119 | 3/2003 |
| WO | 2003046636 | 6/2003 |
| WO | 03/062802 | 7/2003 |
| WO | 03062802 | 7/2003 |
| WO | 2003062802 | 7/2003 |
| WO | 2003105678 | 12/2003 |
| WO | 2004057266 | 7/2004 |
| WO | 2004066824 | 8/2004 |
| WO | 2004088361 | 10/2004 |
| WO | 2004105598 | 12/2004 |
| WO | 2005/047813 | 5/2005 |
| WO | 2005047813 | 5/2005 |
| WO | 2005000115 | 6/2005 |
| WO | 2005054780 | 6/2005 |
| WO | 2006004743 | 1/2006 |
| WO | 2006014392 | 2/2006 |
| WO | 2006039091 | 4/2006 |
| WO | 2006059109 | 6/2006 |
| WO | 2006124860 | 11/2006 |
| WO | 2006130797 | 12/2006 |
| WO | 2007028531 | 3/2007 |
| WO | 2007083138 | 7/2007 |

OTHER PUBLICATIONS

D. Huang et al., "Optical Coherence Tomography," *Science*, vol. 254, pp. 1178-1181, Nov. 1991.

Tearney et al., "High-Speed Phase -and Group Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998.

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, May 1998.

Yung et al., "Phase-Domain Processing of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *Science*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., "A Portable, Low Coherence Interferometry Based Instrument for Fine Needle Aspiration Biopsy Guidance," Accepted to Review of Scientific Instruments, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal Of The Optical Society Of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal Of Lightwave Technology*. vol. 7, pp. 3-10, Jan. 1989.

Beaud, P. et al., "Optical Reflectometry with Micrometer Resolution for the Investigation of Integrated Optical-Devices," *Leee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of America B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues By Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal Of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-303.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, Vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging Of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorovič, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A. Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. (2000). "Technique for Detecting Serial Topographic Changes in the Optic Disc and Peripapillary Retina Using Scanning Laser Tomograph." *Invest. Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Opthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography.* Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of pre-cancer." *Ieee Journal of Quantum Electronics* 38(2): 122-130.

Dettwiller, L. (1997). "Polarization state interference: a general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry.* Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography.* Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd : YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. And R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkami, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jong, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31(7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." *Journal of the Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. M., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth- independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics Part 1-Regular Papers Short Notes & Review Papers* 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti: sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, Methods, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: a comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multifunctional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." *Applied Optics* 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter- endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Journal* 81(5): 2964-2971.

Troy, T. L. and S. N. Thennadil (2001). "Optical properties of human skin in the near infrared wavelength range of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry: an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(13): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. (2002). "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz sensitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." Optics Communications 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of *Xenopus laevis.*" *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13) : 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength- swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter. " *Optics Letters* 28(20): 1981-1983.

Yun, S. H., G. J. Tearney, et al. (2004). "Pulsed-source and swept-source spectral- domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.Clark et al., "Tracking Speckle Patterns with Optical Correlation", *SPIE*, 1992, 1772:77-87.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *American Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim, Acta*, 1986, 45(1/2):S 23-S 27.

T. Yoshimura et al., "Statistical properties of dynamic speckles", *J. Opt. Soc. Am A*. 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

D. Fu et al., "Non-invasive quantitative reconstruction of tissue elasticity using an iterative forward approach", *Phys. Med. Biol.* 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740.

International Written Opinion for International Patent application No. PCT/US2005/039740.

International Search Report for International Patent application No. PCT/US2005/030294.

International Written Opinion for International Patent application No. PCT/US2005/043951.

International Search Report for International Patent application No. PCT/US2005/043951.

Erdelyi et al. "Generation of diffraction-free beams for applications in optical microlithography", *J. Vac. Sci. Technol.* B 15 (12), Mar./Apr. 1997, pp. 287-292.

International Search Report for International Patent application No. PCT/US2005/023664.

International Written Opinion for International Patent application No. PCT/US2005/023664.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704.

International Search Report for International Patent application No. PCT/US2004/039454.

International Written Opinion for International Patent application No. PCT/US2004/039454.

PCT International Preliminary Report on Patentability for International Application No. PCT/US2004/038404 dated Jun. 2, 2006.

Notice of Reasons for Rejection and English translation for Japanese Patent Application No. 2002-538830.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162.

A. Ymeti et al., "Integration of microfluidics with a four-channel integrated optical Young interferometer immunosensor", Biosensors and Bioelectronics, Elsevier Science Publishers, 2005, pp. 1417-1421.

PCT International Search Report for Application No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography", Gastrointestinal Endoscopy clinics of North America, 14 (2004) pp. 573-588.

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.

Ko T et al., "Ultrahigh resolution in vivo versus ex vivo OCT imaging and tissue preservation", Conference on Lasers and electro-optics, 2001, pp. 252-253.

Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.

PCT International Search Report for Application No. PCT/US2006/016677 filed Apr. 28, 2006.

International Written Opinion for International Patent application No. PCT/US2006/016677 filed Apr. 28, 2006.

Office Action dated Nov. 13, 2006 for U.S. Appl. No. 10/501,268.

Office Action dated Nov. 20, 2006 for U.S. Appl. No. 09/709,162.

PCT International Search Report and Written Opinion for Application No. PCT/US2004/023585 filed Jul. 23, 2004.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics 19, 1998, pp. 107-117.

Lauer, V. "New approach to optical diffraction tomography yielding a vector equation of diffraction tomography and a novel tomographic microscope", Journal of Microscopy vol. 205, Issue 2, 2002, pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esophegeal and Gastric Carcinoma in the United States." *American Cancer Society* vol. 83, No. 10 pp. 2049-2053.

Barr, H et al. (2005) "Endoscopic Therapy for Barrett's Oesophaugs" *Gut* vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" *Gastrorenterology* vol. 112, pp. 1787-1797.

Sepchler, Stuart Jon. (1997) "Barrett's Esophagus: Should We Brush off this Balloning Problem?" *Gastroenterology* vol. 112, pp. 2138-2152.

Froehly, J. et al. (2003) "Multiplexed 3D Imaging Using Wavelength Encoded Spectral Interferometry: A Proof of Principle" *Optics Communications* vol. 222, pp. 127-136.

Kubba A.K. et al. (1999) "Role of p53 Assessment in Management of Barrett's Esophagus" *Digestive Disease and Sciences* vol. 44, No. 4. pp. 659-667.

Reid, Brian J. (2001) "p53 and Neoplastic Progression in Barrett's Esophagus" *The American Journal of Gastroenterology* vol. 96, No. 56, pp. 1321-1323.

Sharma, P. et al.(2003) "Magnification Chromoendoscopy for the Detection of Intestinal Metaplasia and Dysplasia in Barrett's Oesophagus" *Gut* vol. 52, pp. 24-27.

Kuipers E.J et al. (2005) "Diagnostic and Therapeutic Endoscopy" *Journal of Surgical Oncology* vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" *Gastroenterology* vol. 120, pp. 1620-1629.

Adrain, Alyn L. et al. (1997) "High-Resolution Endoluminal Sonography is a Sensitive Modality for the Identification of Barrett's Meaplasia" *Gastrointestinal Endoscopy* vol. 46, No. 2, pp. 147-151.

Canto, Marcia Irene et al (1999) "Vital Staining and Barrett's Esophagus" *Gastrointestinal Endoscopy* vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" *Clinical Gastroenterology and Hepatology* vol. 4, pp. 38-3.

Poneros, John M. et al. (2001) "Diagnosis of Specialized Intestinal Metaplasia by Optical Coherence Tomography" *Gastroenterology* vol. 120, pp. 7-12.

Ho, W.Y. et al. (2005) "115 KHz Tuning Repetition Rate Ultrahigh-Speed Wavelength-Swept Semiconductor Laser" *Optics Letters* col. 30, No. 23, pp. 3159-3161.

Brown, Stanley B. et al. (2004) "The Present and Future Role of Photodynamic Therapy in Cancer Treatment" *The Lancet Oncology* vol. 5, pp. 497-508.

Boogert, Jolanda Van Den et al. (1999) "Endoscopic Ablation Therapy for Barrett's Esophagua with High-Grade Dysplasia: A Review" *The American Journal of Gastroenterology* vol. 94, No. 5, pp. 1153-1160.

Sampliner, Richard E. et al. (1996) "Reversal of Barrett's Esophagus with Acid Suppression and Multipolar Electrocoagulation: Preliminary Results" *Gastrointestinal Endoscopy* vol. 44, No. 5, pp. 532-535.

Sampliner, Richard E. (2004) "Endoscopic Ablative Therapy for Barrett's Esophagus: Current Status" *Gastrointestinal Endoscopy* vol. 59, No. 1, pp. 66-69.

Soetikno, Roy M. et al. (2003) "Endoscopic Mucosal resection" *Gastrointestinal Endoscopy* vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" *Gastrointestinal Endoscopy* vol. 60, No. 6, pp. 1002-1010.

Pfefer, Jorje at al. (2006) "Performance of the Aer-O-Scope, A Pneumatic, Self Propelling, Self Navigating Colonoscope in Animal Experiments" *Gastrointestinal Endoscopy* vol. 63, No. 5, pp. AB223.

Overholt, Bergein F. et al. (1999) "Photodynamic Therapy for Barrett's Esophagus: Follow-Up in 100 Patients" *Gastrointestinal Endoscopy* vol. 49, No. 1, pp. 1-7.

Vogel, Alfred et al. (2003) "Mechanisms of Pulsed Laser Ablation of Biological Tissues" *American Chemical Society* vol. 103, pp. 577-644.

McKenzie, A. L. (1990) "Physics of Thermal Processes in Laser-Tissue Interaction" *Phys. Med. Biol* vol. 35, No. 9, pp. 1175-1209.

Anderson, R. Rox et al. (1983) "Selective Photothermolysis Precise Microsurgery by Selective Absorption of Pulsed Radiation" *Science* vol. 220, No. 4596, pp. 524-527.

Jacques, Steven L. (1993) "Role of Tissue Optics and Pulse Duration on Tissue Effects During High-Power Laser Irradiation" *Applied Optics* vol. 32, No. 13, pp. 2447-2454.

Nahen, Kester et al. (1999) "Investigations on Acosustic On-Line Monitoring of IR Laser Ablation of burned Skin" *Lasers in Surgery and Medicine* vol. 25, pp. 69-78.

Jerath, Maya R. et al. (1993) "Calibrated Real-Time Control of Lesion Size Based on Reflectance Images" *Applied Optics* vol. 32, No. 7, pp. 1200-1209.

Jerath, Maya R. et al (1992) "Dynamic Optical Property Changes: Implications for Reflectance Feedback Control of Photocoagulation" *Journal of Photochemical,.Photobiology. B: Biol* vol. 16, pp. 113-126.

Deckelbaum, Lawrence I. (1994) "Coronary Laser Angioplasty" *Lasers in Surgery and Medicine* vol. 14, pp. 101-110.

Kim, B.M. et al. (1998) "Optical Feedback Signal for Ultrashort Laser Pulse Ablation of Tissue" *Applied Surface Science* vol. 127-129, pp. 857-862.

Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.

Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.

Thomsen, Sharon et al. (1990) "Microscopic Correlates of Macroscopic Optical Property Changes During Thermal Coagulation of Myocardium" *SPIE* vol. 1202, pp. 2-11.

Khan, Misban Huzaira et al. (2005) "Intradermally Focused Infrared Laser Pulses: Thermal Effects at Defined Tissue Depths" *Lasers in Surgery and Medicine* vol. 36, pp. 270-280.

Neumann, R.A. et al. (1991) "Enzyme Histochemical Analysis of Cell Viability After Argon Laser-Induced Coagulation Necrosis of the Skin" *Journal of the American Academy of Dermatology* vol. 25, No. 6, pp. 991-998.

Nadkarni, Seemantini K. et al (2005) "Charaterization of Atherosclerotic Plaques by Laser Speckle Imaging" *Circulation* vol. 112, pp. 885-892.

Zimnyakov, Dmitry A. et al (2002) "Speckle-Contrast Monitoring of Tissue Thermal Modification" *Applied Optics* vol. 41, No. 28, pp. 5989-5996.

Morelli, J.G., et al (1986) "Tunable Dye Laser (577 nm) Treatment of Port Wine Stains" *Lasers in Surgery and Medicine* vol. 6, pp. 94-99.

French, P.M.W. et al. (1993) "Continuous-wave Mode-Locked $Cr^{4+:}$ YAG Laser" *Optics Letters* vol. 18, No. 1, pp. 39-41.

Sennaroglu, Alphan at al. (1995) "Efficient Continuous-Wave Chromium-Doped YAG Laser" *Journal of Optical Society of America* vol. 12, No. 5, pp. 930-937.

Bouma, B et al. (1994) "Hybrid Mode Locking of a Flash-Lamp-Pumped Ti: $Al_2O_3$ Laser" *Optics Letters* vol. 19, No. 22, pp. 1858-1860.

Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.

Fernández, Cabrera Delia et al. "Automated detection of retinal layer structures on optical coherence tomography images", *Optics Express* vol. 13, No. 25, Oct. 4, 2005, pp. 10200-10216.

Ishikawa, Hiroshi et al. "Macular Segmentation with optical coherence tomography", Investigative Ophthalmology & Visual Science, vol. 46, No. 6, Jun. 2005, pp. 2012-2017.

Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.

PCT International Search Report and Written Opinion for Application No. PCT/US2006/031905 dated May 3, 2007.

PCT International Search Report and Written Opinion for Application No. PCT/US2007/060481 dated May 23, 2007.

PCT International Search Report and Written Opinion for Application No. PCT/US2007/060717 dated May 24, 2007.

PCT International Search Report and Written Opinion for Application No. PCT/US2007/060319 dated Jun. 6, 2007.

D. Yelin et al., "Three-dimensional imaging using spectral encoding heterodyne interferometry", Optics Letters, Jul. 15, 2005, vol. 30, No. 14, pp. 1794-1796.

Akiba, Masahiro et al. "En-face optical coherence imaging for three-dimensional microscopy", SPIE, 2002, pp. 8-15.

Office Action dated Aug. 10, 2007 for U.S. Appl. No. 10/997,789.

Office Action dated Feb. 2, 2007 for U.S. Appl. No. 11/174,425.

PCT International Search Report and Written Opinion for Application No. PCT/US2007/060657 dated Aug. 13, 2007.

Joo, Chulmin et al., Spectral-domain optical coherence phase microscopy for quantitative phase-contrast imaging, Optics Letters, Aug. 15, 2005, vol. 30, No. 16, pp. 2131-2133.

Guo, Bujin et al., "Laser-based mid-infrared reflectance imaging of biological tissues", Optics Express, Jan. 12, 2004, vol. 12, No. 1, pp. 208-219.

Office Action dated Mar. 28, 2007 for U.S. Appl. No. 11/241,907.

Office Action dated May 23, 2007 for U.S. Appl. No. 10/406,751.

Office Action dated May 23, 2007 for U.S. Appl. No. 10/551,735.

PCT International Search Report and Written Opinion for Application No. PCT/US2007/061815 dated Aug. 2, 2007.

Sir Randall, John et al., "Brillouin scattering in systems of biological significance", Phil. Trans. R. Soc. Lond. A 293, 1979, pp. 341-348.

Takagi, Yasunari, "Application of a microscope to Brillouin scattering spectroscopy", Review of Scientific Instruments, No. 12, Dec. 1992, pp. 5552-5555.

Lees, S. et al., "Studies of Compact Hard Tissues and Collagen by Means of Brillouin Light Scattering", Connective Tissue Research, 1990, vol. 24, pp. 187-205.

Berovic, N. "Observation of Brillion scattering from single muscle fibers", European Biophysics Journal, 1989, vol. 17, pp. 69-74.

PCT International Search Report and Written Opinion for Application No. PCT/US2007/062465 dated Aug. 8, 2007.

Pyhtila John W. et al., "Rapid, depth-resolved light scattering measurements using Fourier domain, angle-resolved low coherence interferometry", Optics Society of America, 2004.

Pyhtila John W. et al., "Determining nuclear morphology using an improved angle-resolved low coherence interferometry system", Optics Express, Dec. 15, 2003, vol. 11, No. 25, pp. 3473-3484.

Desjardins A.E., et al., "Speckle reduction in OCT using massively-parallel detection and frequency-domain ranging", Optics Express, May 15, 2006, vol. 14, No. 11, pp. 4736-4745.

Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-8.

PCT International Search Report and Written Opinion for Application No. PCT/US2007/066017 dated Aug. 30, 2007.

Yamanari M. et al., "Polarization sensitive Fourier domain optical coherence tomography with continuous polarization modulation", Proc. of SPIE, vol. 6079, 2006.

Zhang Jun et al., "Full range polarization-sensitive Fourier domain optical coherence tomography", Optics Express, Nov. 29, 2004, vol. 12, No. 24, pp. 6033-6039.

European Patent Office Search report for Application No. 01991092. 6-2305 dated Jan. 12, 2006.

PCT International Search Report and Written Opinion for Application No. PCT/US2007/060670 dated Sep. 21, 2007.

Office Action dated Oct. 11, 2007 for U.S. Appl. No. 11/534,095.

Office Action dated Oct. 9, 2007 for U.S. Appl. No. 09/709,162.

Notice of Allowance dated Oct. 3, 2007 for U.S. Appl. No. 11/225,840.

Siavash Yazdanfar et al., "In Vivo imaging in blood flow in human retinal vessels using color Doppler optical coherence tomography", SPIE, 1999 vol. 3598, pp. 177-184.

Office Action dated Oct. 30, 2007 for U.S. Appl. No. 11/670,069.

Office Action dated Nov. 15, 2007 for U.S. Appl. No. 11/285,301.

Tang C. L. et al., "Wide-band electro-optical tuning of semiconductor lasers", Applied Physics Letters, vol. 30, No. 2, Jan. 15, 1977, pp. 113-116.

Tang C. L. et al., "Transient effects in wavelength-modulated dye lasers", Applied Physics Letters, vol. 26, No. 9, May 1, 1975, pp. 534-537.

Telle M. John, et al., "Very rapid tuning of cw dye laser", Applied Physics Letters, vol. 26, No. 10, May 15, 1975, pp. 572-574.

Telle M. John, et al., "New method for electro-optical tuning of tunable lasers", Applied Physics Letters, vol. 24, No. 2, Jan. 15, 1974, pp. 85-87.

Wang, Xueding et al., "Propagation of polarized light in birefringent turbid media: time-resolved simulations", Optical Imaging Laboratory, Biomedical Engineering Program, Texas A&M University, 2001.

Smith, P.J., M., E.M.; Taylor, C.M.; Selviah, F.R.; Day, S.E.; Commander, L.G., "Variable-Focus Microlenses as a Potential Technology for Endoscopy", 2001.

Lewis, Neil E., et al. "Applications of Fourier Transform Infrared Imaging Microscopy in Neurotoxicity", Annals New York Academy of Sciences, pp. 234-246, May 1997.

Yabushita, H.B., B.E.; Houser, S.L.; Aretz, H.T.; Jang, I.; Schlendorf, K.H.; Kauffman, C.R.; Shiskov, M.; halpern E.F.; Tearney, G.J., "Measurement of Thin Fibrous Caps in Atherosclerotic Plaques by Optical Coherence Tomography", about Jun. 25, 2002.

Barfuss et al. (1989), "Modified Optical Frequency Domain Reflectometry with High Spatial Resolution for Components of Integrated Optic Systems", Journal of Light Technology, IEEE, vol. 7., No. 1.

Yun et al., (2004), "Removing the Depth-Degeneracy in Optical Frequency Domain Imaging with Frequency Shifting", Optics Express, vol. 12, No. 20.

Office Action dated Aug. 18, 2009 for U.S. Appl. No. 12/277,178.

Office Action dated Aug. 13, 2009 for U.S. Appl. No. 10/136,813.

Office Action dated Aug. 6, 2009 or U.S. Appl. No. 11 624,455.

Liptak David C. et al., (2007) "On the Development of a Confocal Rayleigh-Brillouin Microscope" *American Institute of Physics* vol. 78, 016106.

Office Action mailed Oct. 1, 2008 for U.S. Appl. No. 11/955,986.

Invitation of Pay Additional Fees mailed Aug. 7, 2008 for International Application No. PCT/US2008/062354.

Invitation of Pay Additional Fees mailed Jul. 20, 2008 for International Application No. PCT/US2007/081982.

International Search Report and Written Opinion mailed Mar. 7, 2006 for PCT/US2005/035711.

International Search Report and Written Opinion mailed Jul. 18, 2008 for PCT/US2008/057533.

Aizu, Y et al. (1991) "Bio-Speckle Phenomena and Their Application to the Evaluation of Blood Flow" Optics and Laser Technology, vol. 23, No. 4, Aug. 1, 1991.

Richards G.J. et al. (1997) "Laser Speckle Contrast Analysis (LASCA): A Technique for Measuring Capillary Blood Flow Using the First Order Statistics of Laser Speckle Patterns" Apr. 2, 1997.

Gonick, Maria M., et al (2002) "Visualization of Blood Microcirculation Parameters in Human Tissues by Time Integrated Dynamic Speckles Analysis" vol. 972, No. 1, Oct. 1, 2002.

International Search Report and Written Opinion mailed Jul. 4, 2008 for PCT/US2008/051432.

Jonathan, Enock (2005) "Dual Reference Arm Low-Coherence Interferometer-Based Reflectometer For Optical Coherence Tomography (OCT) Application" *Optics Communications* vol. 252.

Motaghian Nezam, S.M.R. (2007) "increased Ranging Depth in optical Frequency Domain Imaging by Frequency Encoding" *Optics Letters*, vol. 32, No. 19, Oct. 1, 2007.

Office Action dated Jun. 30, 2008 for U.S. Appl. No. 11/670,058.

Office Action dated Jul. 7, 2008 for U.S. Appl. No. 10/551,735.

Australian Examiner's Report mailed May 27, 2008 for Australian patent application No. 2003210669.

Notice of Allowance mailed Jun. 4, 2008 for U.S. Appl. No. 11/174,425.

European communication dated May 15, 2008 for European patent application No. 05819917.5.

International Search Report and Written Opinion mailed Jun. 10, 2008 for PCT/US2008/051335.

Oh. W.Y. et al (2006) "Ultrahigh-Speed Optical Frequency Domain Imaging and Application to laser Ablation Monitoring" *Applied Physics Letters*, vol. 88.

Office Action dated Aug. 21, 2008 for U.S. Appl. No. 11/505,700.

Sticker, Markus (2002) En Face Imaging of Single Cell layers by Differential Phase-Contrast Optical Coherence Microscopy) *Optics Letters*, col. 27, No. 13, Jul. 1, 2002.

International Search Report and Written Opinion dated Jul. 17, 2008 for International Application No. PCT/US2008/057450.

International Search Report and Written Opinion dated Aug. 11, 2008 for International Application No. PCT/US2008/058703.

US National Library of Medicine (NLM), Bethesda, MD, US; Oct. 2007 (Oct. 2007), "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Patent Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1. Ω.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy" ΩΩ.
Database Biosis Biosciences Information Service, Philadelphia, PA, US; Oct. 2006, Yelin D. et al: "Three-Dimensional Miniature Endoscopy" ΩΩ.
International Search Report and Written Opinion mailed Mar. 14, 2005 for PCT/U52004/018045.
Notification of the international Preliminary Report on Patentability mailed Oct. 21, 2005.
Shim M.G. et al., "Study of Fiber-Optic Probes for In vivo Medical Raman Spectroscopy" Applied Spectroscopy. vol. 53, No. 6, Jun. 1999 ΩΩΩ.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005 ΩΩΩ.
Jun Zhang et al. "Full Range Polarization-Sensitive Fourier Domain Optical Coherence Tomography" Optics Express, vol. 12, No. 24. Nov. 29, 2004 ΩΩΩΩ.
Yonghua et al., "Real-Time Phase-Resolved Functional Optical Hilbert Transformation" Optics Letters, vol. 27, No. 2, Jan. 15, 2002 ΩΩΩΩ.
Siavash et al., "Self-Referenced Doppler Optical Coherence Tomography" Optics Letters, vol. 27, No. 23, Dec. 1, 2002 ΩΩΩΩ.
International Search Report and Written Opinion dated Dec. 20, 2004 for PCT/USO4/10152.
Notification Concerning Transmittal of Copy of International Preliminary Report on Patentability dated Oct. 13, 2005 for PCT/US04/10152.
International Search Report and Written Opinion dated Mar. 23, 2006 for PCT/US2005/042408.

International Preliminary Report on Patentability dated Jun. 7, 2007 for PCT/US2005/042408.
International Search Report and Written Opinion dated Feb. 28, 2007 for International Application No. PCT/US2006/038277 ΩΩΩΩΩΩ.
International Search Report and Written Opinion dated Jan. 30, 2009 for International Application No. PCT/US2008/081834ΩΩΩΩΩΩΩΩ.
International Search Report and Written Opinion dated Feb. 2, 2009 for International Application No. PCT/US2008/071786 ΩΩΩΩΩΩΩΩ.
Bilenca A et al: "The Role of Amplitude and phase in Fluorescence Coherence Imaging: From Wide Filed to Nanometer Depth Profiling", *Optics IEEE*, May 5, 2007 ΩΩΩΩΩΩΩΩΩ.
Inoue, Yusuke et al: "Varible Phase-Contrast Fluorescence Spectrometry for Fluorescently Strained Cells", *Applied Physics Letters*, Sep. 18, 2006 ΩΩΩΩΩΩΩΩ.
Bernet, S et al: "Quantitative Imaging of Complex Samples by Spiral Phase Contrast Microscopy", *Optics Express*, May 9, 2006 ΩΩΩΩΩΩΩΩΩ.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems ", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.
International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.

* cited by examiner

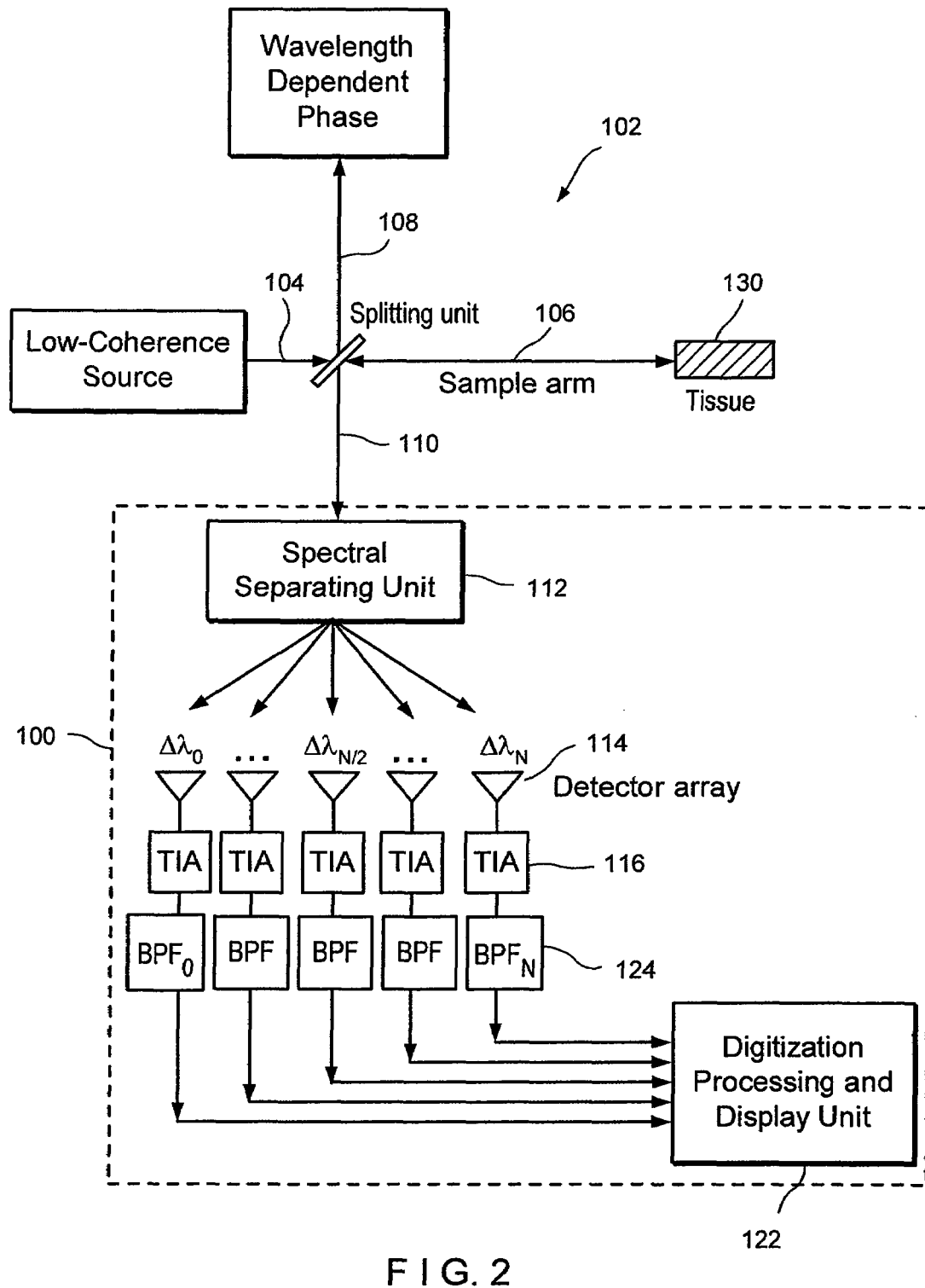
F I G. 2

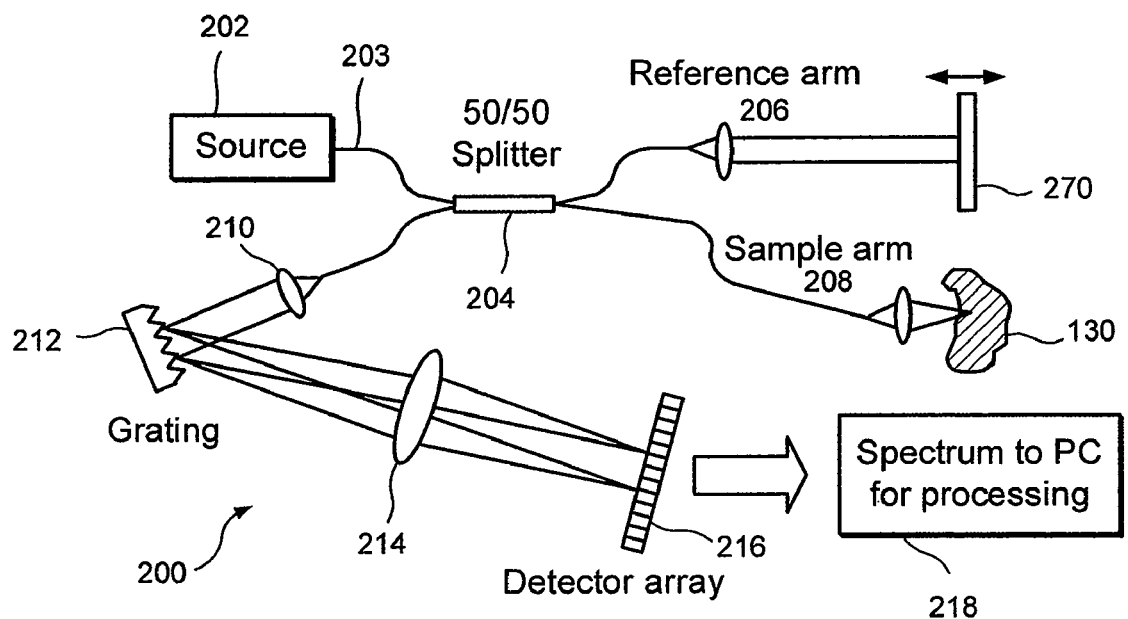
F I G. 3
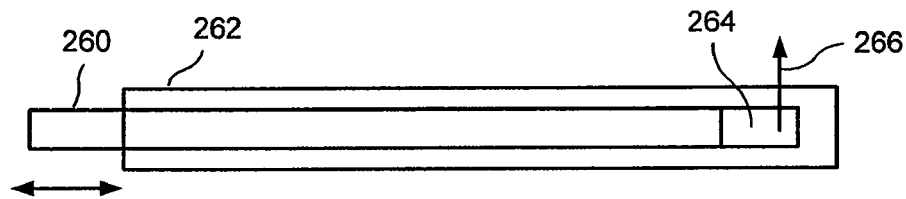
F I G. 4

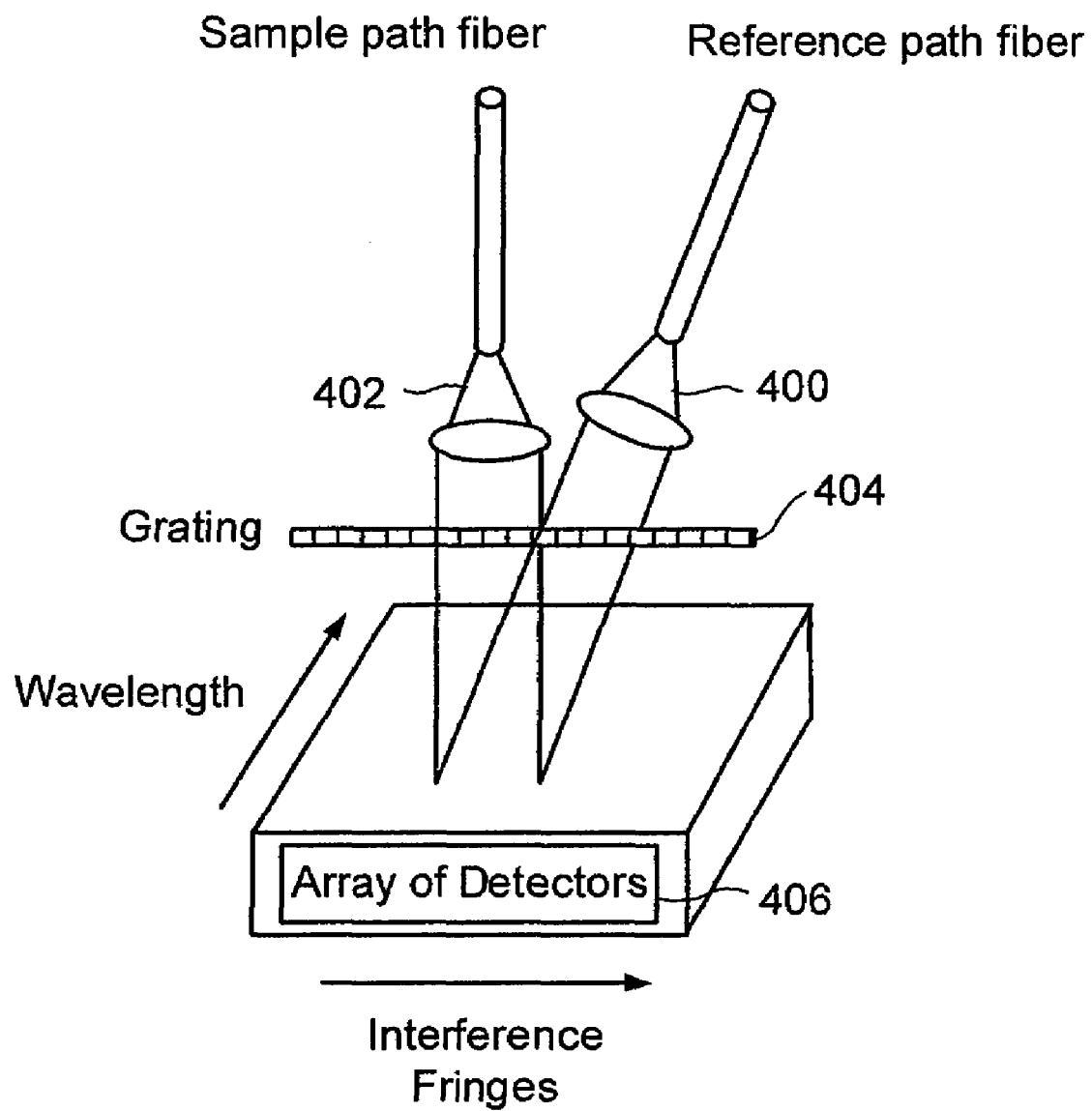
F I G. 9

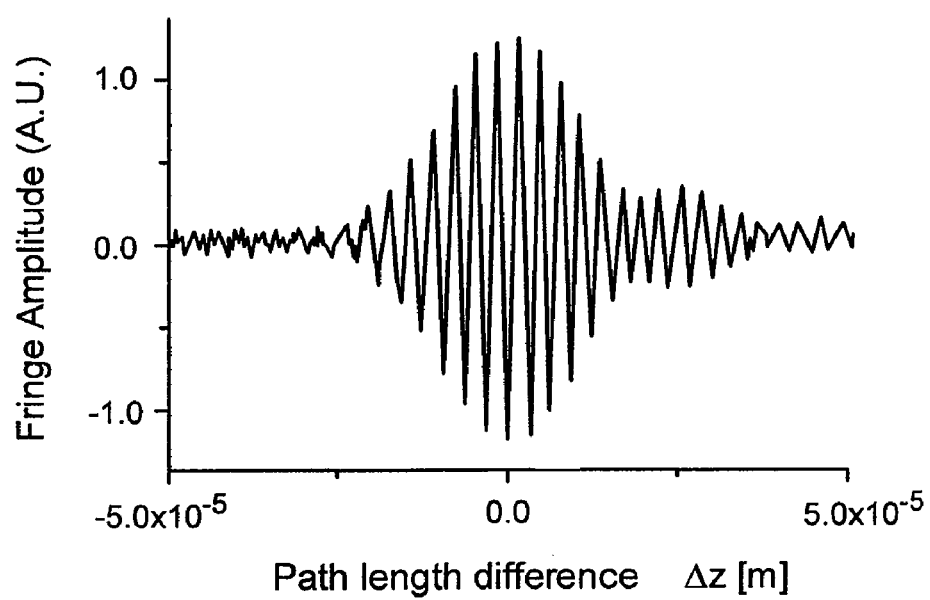
F I G. 14

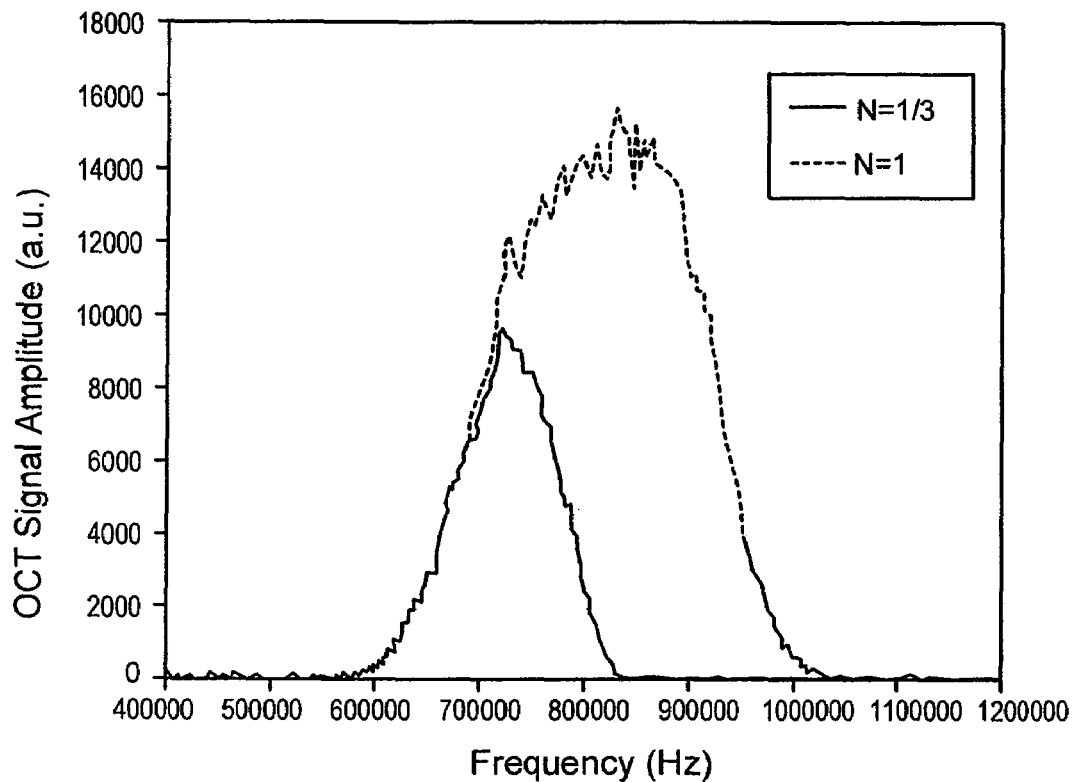
F I G. 17
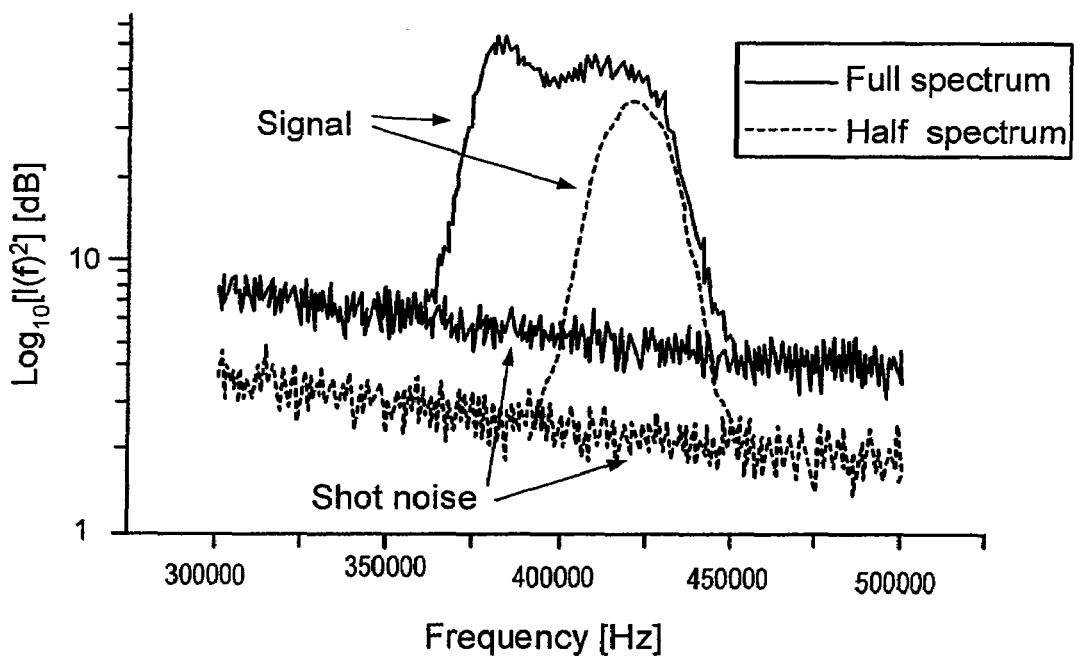
F I G. 18

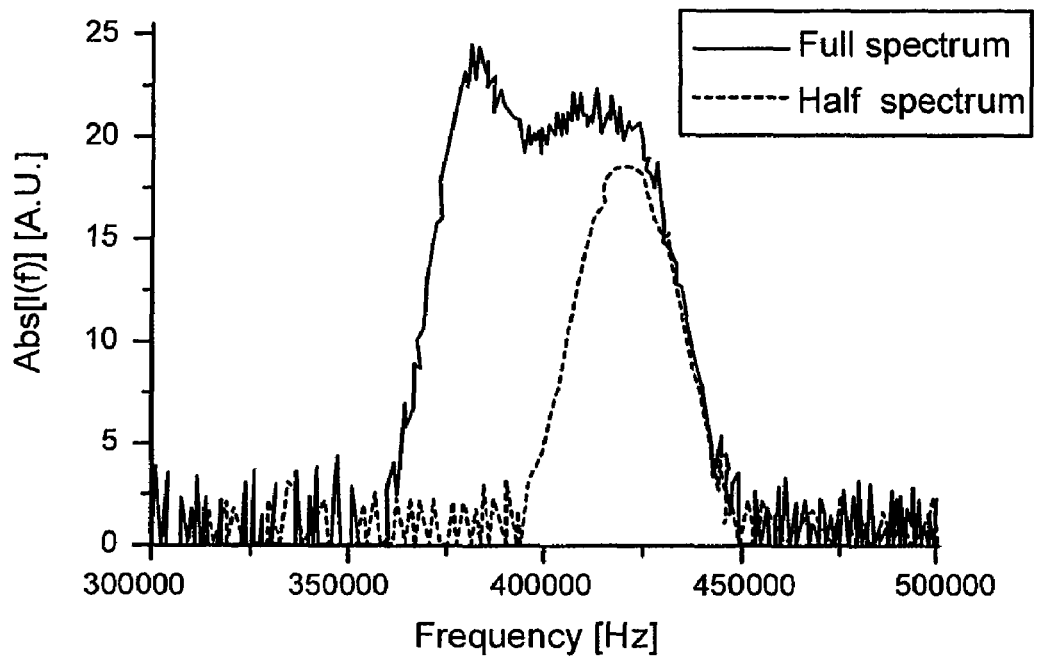
F I G. 19
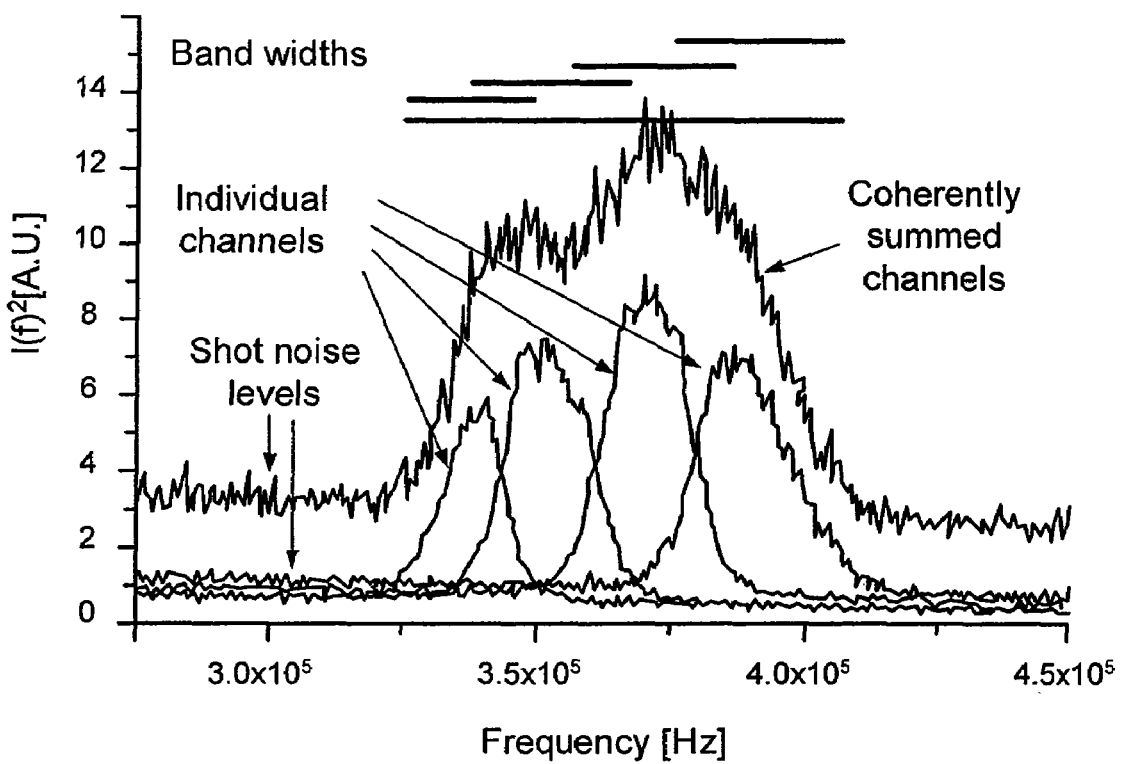
F I G. 20

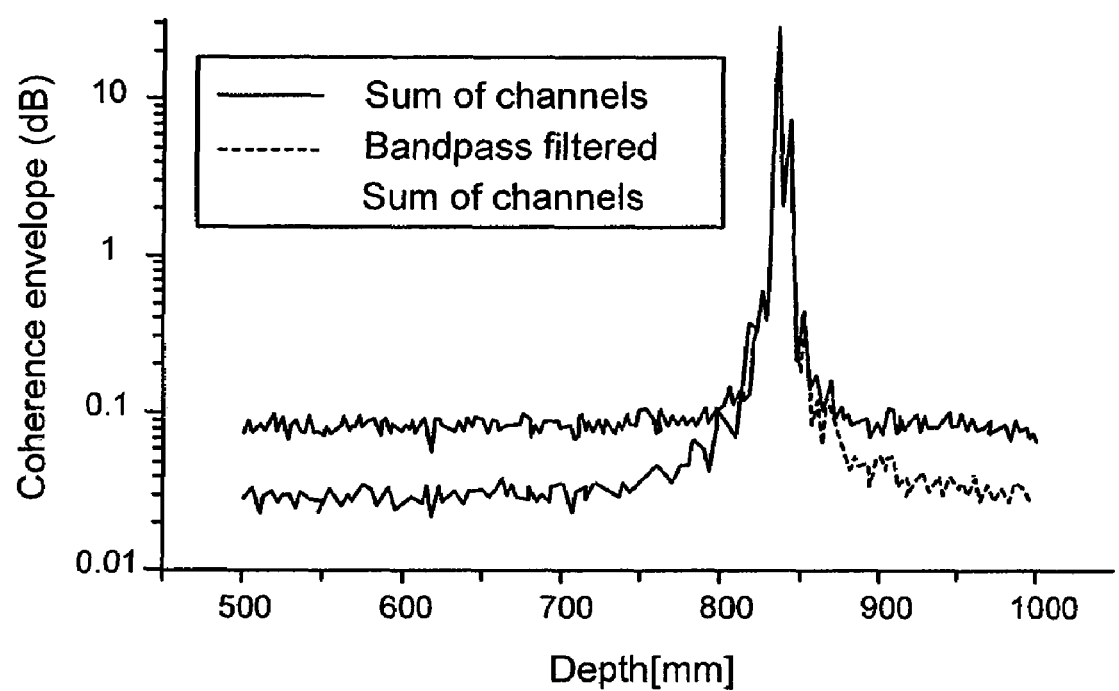
F I G. 21

APPARATUS AND METHOD FOR RANGING AND NOISE REDUCTION OF LOW COHERENCE INTERFEROMETRY LCI AND OPTICAL COHERENCE TOMOGRAPHY OCT SIGNALS BY PARALLEL DETECTION OF SPECTRAL BANDS

CROSS-REFERENCE TO RELATED APPLICATIONS

The present application is a divisional of U.S. patent application Ser. No. 10/501,276, filed Jul. 9, 2004, now U.S. Pat No. 7,355,716 which is U.S. National Phase of International Application No. PCT/US03/02349 filed Jan. 24, 2003. This application also claims benefit of U.S. provisional patent application No. 60/351,904, filed Jan. 24, 2002, entitled APPARATUS AND METHOD FOR RANGING AND SHOT NOISE REDUCTION OF LOW COHERENCE INTERFEROMETRY (LCI) AND OPTICAL COHERENCE TOMOGRAPHY (OCT) SIGNALS BY PARALLEL DETECTION OF SPECTRAL BANDS, and copending U.S. application Ser. No. 10/136,813, filed Apr. 30, 2002, entitled METHOD AND APPARATUS FOR IMPROVING IMAGE CLARITY AND SENSITIVITY IN OPTICAL COHERENCE TOMOGRAPHY USING DYNAMIC FEEDBACK TO CONTROL FOCAL PROPERTIES AND COHERENCE GATING, both commonly assigned to the assignee of the present application. The disclosures of all these applications are incorporated herein by reference in their entireties.

FIELD OF THE INVENTION

The present invention relates to apparatus and a method for dramatically increasing the sensitivity in the detection of optical coherence tomography and low coherence interferometry signals by detecting a parallel set of spectral bands, each band being a unique combination of optical frequencies.

BACKGROUND OF THE ART

Two methods currently exist to implement depth ranging in turbid media. The first method is known as Low Coherence Interferometry ("LCI"). This method uses a scanning system to vary the reference arm length and acquire the interference signal at a detector and demodulating the fringe pattern to obtain the coherence envelope of the source cross correlation function. Optical coherence tomography ("OCT") is a means for obtaining a two-dimensional image using LCI. OCT is described by Huang et al. in U.S. Pat. No. 5,321,501. Multiple variations on OCT have been patented, but, many suffer from less than optimal signal to noise ratio ("SNR"), resulting in non-optimal resolution, low imaging frame rates, and poor depth of penetration.

A second method for depth ranging in turbid media is known in the literature as spectral radar. In spectral radar the real part of the cross spectral density of sample and reference arm light is measured with a spectrometer. Depth profile information is encoded on the cross-spectral density modulation. Prior art for spectral radar is primarily found in the literature. U.S. Pat. No. 5,491,552 discloses a spectral radar invention which employs a variation of this technique. The use of spectral radar concepts to increase the signal to noise ratio of LCI and OCT have been described earlier. However, in this description, only the real part of the complex spectral density is measured and the method requires a large number of detector elements (~2,000) to reach scan ranges on the order of a millimeter. It would be desirable to have a method that would allow for an arbitrary number of detector elements. Secondly, the previously described method uses a charge coupled device ("CCD") to acquire the data, which requires a reduction of the reference arm power to approximately the same level as the sample arm power. As a result, large integration times are needed to achieve the SNR improvement. Since no carrier is generated, the 1/f noise will dominate the noise in this system. Power usage is a factor in such imaging techniques. For example in ophthalmic uses, only a certain number of milliwatts of power is tolerable before thermal damage can occur. Thus, boosting power is not feasible to increase SNR in such environments. It would be desirable to have a method of raising the SNR without appreciably increasing power requirements.

SUMMARY OF THE INVENTION

The present invention increases the SNR of LCI and OCT by splitting the LCI broad bandwidth source into N spectral bands. The N spectral bands are individually detected and processed to provide an increase in the SNR by a factor of N. This increase in SNR enables LCI or OCT imaging by a factor of N times faster, or alternatively allows imaging at the same speed with a source that has N times lower power. As a result, the present invention overcomes two of the most important shortcomings of LCI and OCT, i.e., source availability and scan speed. The factor N may reach more than 1,000, and allows construction of OCT and LCI systems that can be more than three orders of magnitude improved from OCT and LCI technology currently in practice.

The present invention enables a breakthrough in current data acquisition speeds and availability of sources for OCT. The shot noise reduction allows for much lower source powers, or much higher acquisition rates than current systems. Limitations in current data acquisition rates (approximately 4 frames/sec) are imposed by available source power. An increase in the sensitivity of the detection by a factor of 8 would allow real time imaging at a speed of 30 frames per second. An increase of the sensitivity by a factor of 1,000-2,000 would allow for the use of sources with much lower powers and higher spectral bandwidths which are readily available, cheaper to produce, and can generate broader bandwidths.

For ophthalmic applications of OCT, the efficient detection would allow for a significant increase of acquisition speed. The limitation in ophthalmic applications is the power that is allowed to enter the eye according to the ANSI standards (approximately 700 microwatts at 830 nm). Current data acquisition speed in ophthalmic applications is approximately 100-500 A-lines per second. The power efficient detection would allow for A-line acquisition rates on the order of 100,000 A-lines per second, or video rate imaging at 3,000 A-lines per image.

In summary, the present invention represents a greatly improved means for performing LCI and OCT, and as a result, would be of great interest to entities considering developing LCI and OCT diagnostic technologies for medical and non-medical applications.

Other features and advantages of the present invention will become apparent upon reading the following detailed description of embodiments of the invention, when taken in conjunction with the appended claims.

BRIEF DESCRIPTION OF THE DRAWINGS

The invention is illustrated in the drawings in which like reference characters designate the same or similar parts throughout the figures of which:

FIG. 2 is a schematic view of a preferred embodiment of a standalone system

FIG. 3 is a schematic view showing spectral demultiplexing into 2 bands.

FIG. 4 is a schematic of spectral demultiplexing into 4 bands. The spectral resolution required for each detector is twice as course as in the case of multiplexing into 2 bands.

FIG. 9 is a schematic view of using beam recombination to provide one dimension of interference information along one dimension of a two-dimensional detector array, while performing wavelength demultiplexing along the other dimension of the two dimensional array.

FIG. 14 is a graph of a typical interference patter as a function of path length difference between sample arm and reference arm.

FIG. 17 is a graph of frequency versus amplitude spectrum substracted from the shot noise (experimental data) for the N=1 (dotted line) and N=1/3 (solid line) cases.

FIG. 18 is a graph of power density for the full spectrum as a function of frequency.

FIG. 19 is a graph after subtraction of the shot noise levels.

FIG. 20 is a graph after processing the signals.

FIG. 21 is a graph of the coherence envelope for the coherently summed channels.

DETAILED DESCRIPTION OF THE PREFERRED EMBODIMENTS

Background

Figure 1:
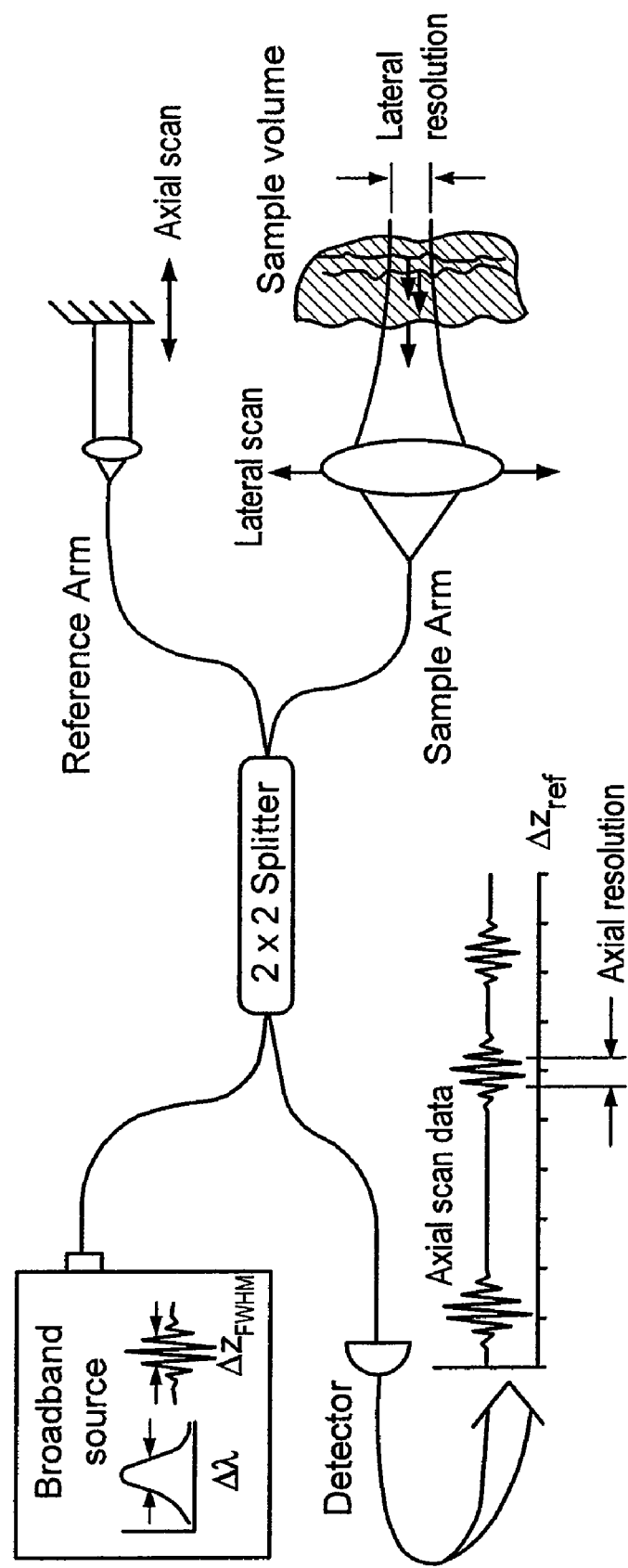
FIG. 1 is a schematic view of a preferred embodiment of the parallel detection scheme for LCI.

The present invention describes a hybrid method that implements aspects of LCI and OCT where the reference arm is scanned, and spectral radar, which does not require reference arm scanning. The signal in the detection arm of an OCT system is split into more than one spectral band before detection. Each spectral band is detected by a separate photo detector and amplified. For each spectral band the signal is band pass filtered around the signal band by analog electronics and digitized, or, alternatively, the signal may be digitized and band pass filtered in software. As a consequence, the shot noise contribution to the signal is reduced by a factor equal to the number of spectral bands. The signal remains the same.

The reduction of the shot noise increases the dynamic range and sensitivity of the system. In the limit of many detectors, no ranging or reference arm scanning is required and the method is similar to spectral radar except that phase information of the cross spectral density is preserved.

Theory

In current OCT system, the recombined light of sample and reference arm is detected by a single detector. The signal is determined by the interference of light reflected from sample and reference arm. For a single object in the sample arm, the OCT signal is proportional to the real part of the Fourier transform of the source spectrum S(k), $$R(\Delta z) \propto \mathrm{Re} \int \exp(ik\Delta z) S(k) dk, \quad (1)$$

with $k=2\pi/\lambda=\omega/c$ the free space wave number and $\Delta z=z-z'$ the path length difference between reference and sample waves respectively. R(z) is the interference part of the signal detected at the photo detectors. The intensity I(z) backscattered from the sample arm at location z is proportional to the square of the envelope of R(z), $I(z) \propto R^2(z)$.

Converting path length difference $\Delta z$ to time difference $\tau$ between arrival of reference and sample waves, $\tau=\Delta z/c$ and using that the time difference $\tau$ is given by measurement time t times twice the speed of the reference mirror v divided by the speed of light c, $\tau=2vt/c$, we obtain, $$R(t) \propto \mathrm{Re} \int \exp(i\omega t v/c) S(\omega) d\omega, \quad (2)$$

with t the measurement time.

Fourier transforming the depth profile R(t), the frequency spectrum of the signal is obtained, $$|R(\omega)| \propto |S(\omega c/v)|, \quad (3)$$

This demonstrates that each angular frequency of the light source or equivalently each wavelength of the source is represented at its own frequency in the measured interferometric signal. The depth profile information R(t) can be obtained from the complex cross spectral density R(ω) by a Fourier transform.

The complex cross spectral density can also be obtained by splitting the signal R(t) in several spectral bands by means of a dispersive or interferometric element. At each detector, only part of the complex cross spectral density is determined. Combining the cross spectral densities of each detector, the full spectral density of the signal is retrieved.

Thus, the same information can be obtained by separating spectral components to individual detectors. Combining the signal of all detectors in software or hardware would result in the same signal as obtained with a single detector. However, a careful analysis of the noise present at each frequency in the case of many individual detectors, reveals that the shot noise contribution is significantly lower, leading to a significant signal to noise improvement. The signal to noise improvement is linearly dependent on the number of spectral bands in which the signal is split. Thus, two spectral bands give a signal to noise improvement of a factor of 2, four spectral bands give a signal to noise improvement of a factor of 4, etc.

Signal to Noise Analysis of Optical Coherence Tomography Signals in the Frequency Domain For a single reflector in the sample arm, the interference fringe signal as a function of position is given by $$R(\Delta z) \propto \operatorname{Re} \int \exp(ik\Delta z) S(k) dk,$$

or equivalently as a function of time, $$R(t) \propto \operatorname{Re} \int \exp(i\omega t v/c) S(\omega) d\omega$$

The coherence envelope peak value is found by setting $\Delta z=0$ or $t=0$;

$$I_{peak} \propto \int S(k) dk \propto \int S(\omega) d\omega$$

In the frequency domain, the Fourier transform of $R(t)$ is given by $$R(\omega) = \int R(t) e^{i\omega t} dt = \int \operatorname{Re} \int \exp(i\omega' t v/c) S(\omega') d\omega' e^{i\omega t} dt = S(\omega c/v)$$

The peak value is given by $$I_{peak} \propto \int R(\omega) d\omega = \int S(\omega c/2v) d\omega$$

In terms of electrical power, the signal is defined as $I_{peak}^2$. In the frequency domain, the signal is, $$I_{peak}^2 \propto \left[\int R(\omega) d\omega\right]^2 = \left[\int S(\omega c/2v) d\omega\right]^2$$

or in terms of sample and reference arm power, $$I_{peak}^2 \propto \left[\int \sqrt{S_{ref}(\omega c/2v)} * \sqrt{S_{sample}(\omega c/2v)} \, d\omega\right]^2 =$$

$$a(z) \left[\int S_{ref}(\omega c/2v) d\omega\right]^2,$$

with $S_{sample}(\omega c/2v) = a(z) S_{ref}(\omega c/2v)$ and $a(z)$ the reflectivity at $z$.

Thus, the signal is proportional to $$a(z) \left[\int S_{ref}(\omega c/2v) d\omega\right]^2.$$

The total power $P_{ref}$ is given by $$P_{ref} = \int S_{ref}(\omega c/2v) d\omega$$

The shot noise has a white noise distribution and the shot noise density is proportional to the total power on the detector $$N_{shot}(\omega) \propto \int S_{ref}(\omega c/2v) d\omega = P_{ref}$$

The shot noise density is given in units [$W^2$/Hz], [$A^2$/Hz] or [$V^2$/Hz]. The total shot noise that contributes to the noise is the Shot noise density multiplied with the bandwidth BW, $N_{shot} = P_{ref} * BW$ Using the above expressions for the Signal and Noise, the SNR ratio for a single detector is given by $$SNR \propto a(z) \left[\int S_{ref}(\omega c/2v) d\omega\right]^2 / P_{ref} * BW = P_{sample} / BW.$$

For a two detector configuration, where the spectrum is equally split over two detectors, the bandwidth BW per detector is half, as is the reference power. For an individual detector in the two detector configuration the signal is given by an integration over half the signal bandwidth, $$a(z) \left[\int_{0.5*BW} S_{ref}(\omega c/2v) d\omega\right]^2.$$

The noise is given by $0.5 * P_{ref} * 0.5 * BW$ and the SNR is now $$SNR \propto a(z) \left[\int_{0.5BW} S_{ref}(\omega c/2v) d\omega\right]^2 / 0.5 P_{ref} * 0.5 BW = P_{sample} / BW.$$

The SNR is the same as in the previous case where the full spectrum was detected by a single detector.

To evaluate the Signal to noise for two detectors simultaneously, the signals of both detectors are coherently added after digital or analog band pass filtering, i.e., after Fourier transforming of the signal $R(t)$ the frequency components $R(\omega)$ within the signal band of each detector are added to form the total signal in the frequency domain. The signal is, $$I_{peak}^2 \propto a(z) \left[\int_{0.5BW} S_{ref}(\omega c/2v) d\omega + \int_{0.5BW} S_{ref}(\omega c/2v) d\omega\right]^2 = a(z) \left[\int_{BW} S_{ref}(\omega c/2v) d\omega\right]^2,$$

which is equal to the signal if all the light was detected by a single detector.

The Noise is the sum of the noise at each detector. The individual detector noise was $N_{shot} = 0.5 * P_{ref} * 0.5 * BW$. The sum of the noise of both detectors is $N_{shot} = 0.5 * P_{ref} * BW$ and the noise is half of what it was if the full spectrum or all the light was detected by a single detector. The SNR ratio in the case when each detector detects half the spectrum and the signal is coherently combined is, $$SNR \propto \alpha(z)[\int S_{ref}(\omega c/2v)d\omega]^2/0.5 \cdot P_{ref} \cdot BW = 2P_{sample}/BW$$

Thus, the SNR is twice as high compared to if the full spectrum or all the light was detected by a single detector.

The gain in SNR is achieved because the shot noise has a white noise spectrum. An intensity present at the detector at frequency ω (or wavelength λ) contributes only to the signal at frequency ω, but the shot noise is generated at all frequencies. By narrowing the optical band width per detector, the shot noise contribution at each frequency is reduced, while the signal component remains the same.

Redundant SNR Arguments

The signal to noise can also be evaluated per frequency. The total SNR is given by, $$SNR \propto \left[\int \sqrt{SNR(\omega)}\,d\omega\right]^2 = \frac{a(z)}{P_{ref} * BW}\left[\int S_{ref}(\omega c/2v)d\omega\right]^2$$

which defines a SNR density as $$\sqrt{SNR(\omega)} \propto S_{ref}(\omega c/2v)\sqrt{\alpha(z)}/\sqrt{P_{ref} * BW},$$

which demonstrates that the SNR density at a particular frequency depends on the total pass band (BW) and the reference power of the signal at the particular detector.

For two detectors, where the spectrum is equally split over two detectors, the bandwidth BW is half, as is the reference power. For an individual detector in the two detector configuration the SNR density is given by, $$\sqrt{SNR(\omega)} \propto S_{ref}(\omega c/2v)\sqrt{\alpha(z)}/\sqrt{0.5P_{ref} * 0.5BW}$$

From the above equation, it is clear that the SNR density increases as the spectral bandwidth at the detector is decreased.

One embodiment of the system of the present invention is shown in FIG. 1. The basic embodiment is an interferometer with a source arm, a sample arm, a reference arm, and a detection arm with a spectral demultiplexing unit, multiple detectors, optional analog processing electronics, and A/D conversion of all signals. The processing and display unit has optionally digital band pass filtering, Digital Fast Fourier Transforms ("FFT's"), coherent combination of signals, and data processing and display algorithms. The detector array may be 1×N for simple intensity ranging and imaging, 2×N for dual balanced detection, 2×N for polarization and/or Doppler sensitive detection, or 4×N for combined dual balanced and polarization and/or Doppler sensitive detection. Alternatively, an M×N array may be used for arbitrary M to allow detection of transverse spatial information on the sample.

Sources

The source arm contains a spatially coherent source that is used to illuminate the interferometer with low-coherence light. The source temporal coherence length is preferably shorter than a few microns (range is about 0.5 μm-30 μm). Examples of sources include, but are not limited to, semiconductor optical amplifier, superluminescent diodes, light-emitting diodes, solid-state femtosecond sources, amplified spontaneous emission, continuum sources, thermal sources, combinations thereof and the like.

Interferometer

The sample arm collects light reflected from the specimen and is combined with the light from the reference arm to form interference fringes. The reference arm reflects light back to be combined with the reference arm. This action of beam splitting/recombining may be performed using a beam splitter (Michelson), or circulator(s) (Mach-Zehnder) or other means known to those skilled in the art for separating a beam into multiple paths and recombining these multiple beams in a manner that interference between the beams may be detected. The splitting may be accomplished in free space or by using passive fiber optic or waveguide components.

Sample Arm

For LCI applications, the sample arm may be terminated by an optical probe comprising an cleaved (angled, flat, or polished) optical fiber or free space beam. A lens (aspherical, gradient index, spherical, diffractive, ball, drum) may be used to focus the beam on or within the sample. Beam directing elements may also be contained within the probe (mirror, prism, diffractive optical element) to direct the focused beam to a desired position on the sample. For OCT applications, the position of the beam may be changed on the sample as a function of time, allowing reconstruction of a two-dimensional image. Altering the position of the focused beam on the sample may be accomplished by a scanning mirror (such as, but not limited to, a galvanometer or piezoelectric actuator), electrooptic actuator, moving the optical fiber (rotating the optical fiber, or linearly translating the optical fiber). The sample arm probe may be a fiber optic probe that has an internally moving element where the motion is initiated at a proximal end of the probe and the motion is conveyed by a motion transducing means (such as, but not limited to, wire, guidewire, speedometer cable, spring, optical fiber and the like) to the distal end. The fiber optic probe may be enclosed in a stationary sheath which is optically transparent where the light exits the probe at the distal end.

Reference Arm Delay

A delay mechanism in the reference arm allows for scanning the length or the group velocity of the reference arm. This delay is produced by stretching ah optical fiber, free space translational scanning using a piezoelectric transducer, or via a grating based pulse shaping optical delay line. As opposed to traditional LCI or OCT systems described in prior art, the reference arm in the present invention does not necessarily need to scan over the full ranging depth in the sample, but is required to scan over at least a fraction of the ranging depth equal to one over the number of detectors. This feature of the present invention is fundamentally different from delay scanning schemes used in LCI and OCT systems disclosed in prior art. The delay line optionally has a mechanism for generating a carrier frequency such as an acoustooptic modulator, electrooptic phase modulator or the like. In order to reduce the scan range of the reference arm, the spectrum needs to be split into spectral bands according to a method that will be explained below.

Detection

In the detection arm a spectral demultiplexing unit demultiplexes the spectral components to separate detectors. The detectors may consist of photodiodes (such as, but not limited to, silicon, InGaAs, extended InGaAs, and the like).

Alternatively, a one or two dimensional array of detectors (such as, but not limited to, photodiode array, CCD, CMOS array, active CMOS array, CMOS "smart pixel" arrays, combinations thereof and the like) may be employed for detection. Two detectors for each spectral band may be used for polarization sensitive detection following separation of the recombined light into orthogonal polarization eigenstates. Detector arrays may be 1×N for simple intensity ranging and imaging, 2×N for dual balanced detection, 2×N for polarization and/or Doppler sensitive detection, or 4×N for combined dual balanced and polarization and/or Doppler sensitive detection. Alternatively, an M×N array may be used for arbitrary M to allow detection of transverse spatial information on the sample.

Detector signals are amplified by Trans Impedance Amplifiers ("TIA's"), band pass filtered (digitally or using analog circuitry) and digitized by A/D converters and stored in a computer for further processing. Each detector is preferably configured to be shot noise limited. Shot noise limited detection is achieved by adjusting the intensity of light returned from the reference arm so that the shot noise dominates over the thermal noise of the resistor in the TIA and is higher than the relative intensity noise ("RIN"). Each detector is balanced for such dual noise reduction.

In a broad aspect of the present invention, the number of detectors, N, can range from 2-10,000 or more. A preferred range of N is about 8-10,000 detectors. In one preferred embodiment, eight detectors (or a number in that area) can provide real time, or close to real time, imaging. When more than about one hundred detectors are used, it is likely that a custom array would need to be constructed.

Figure 8:
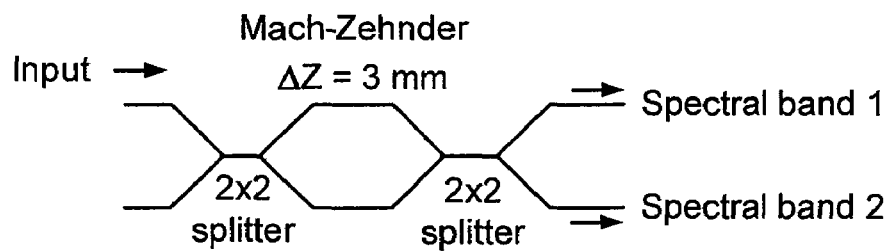
FIG. 8 is a schematic view of demultiplexing unit in combination with two integrating CCD arrays for detection of the dual-balanced wavelength demultiplexed signal.
Figure 10:
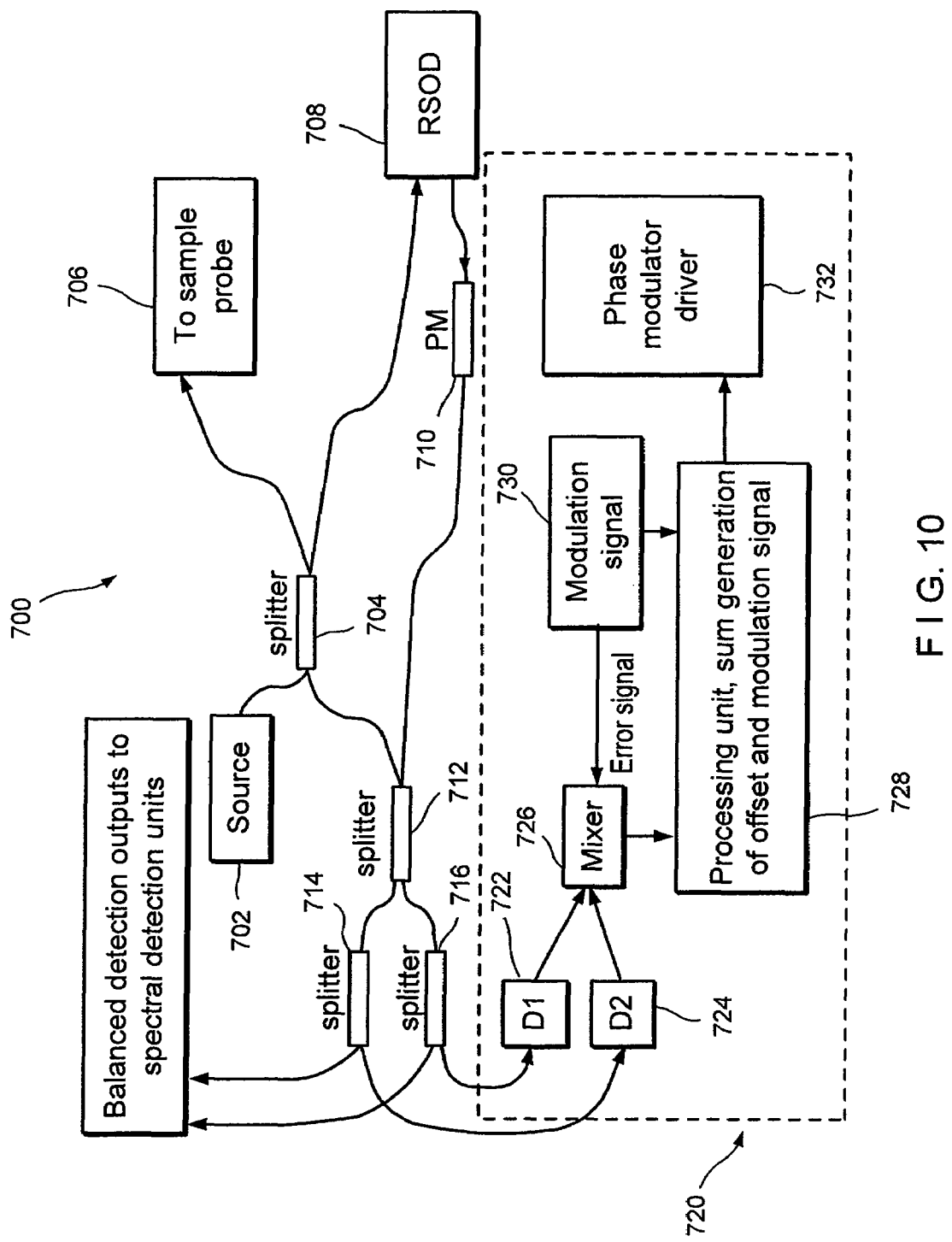
FIG. 10 is a schematic view of a phase tracking system according to one embodiment of the present invention.
Figure 11:
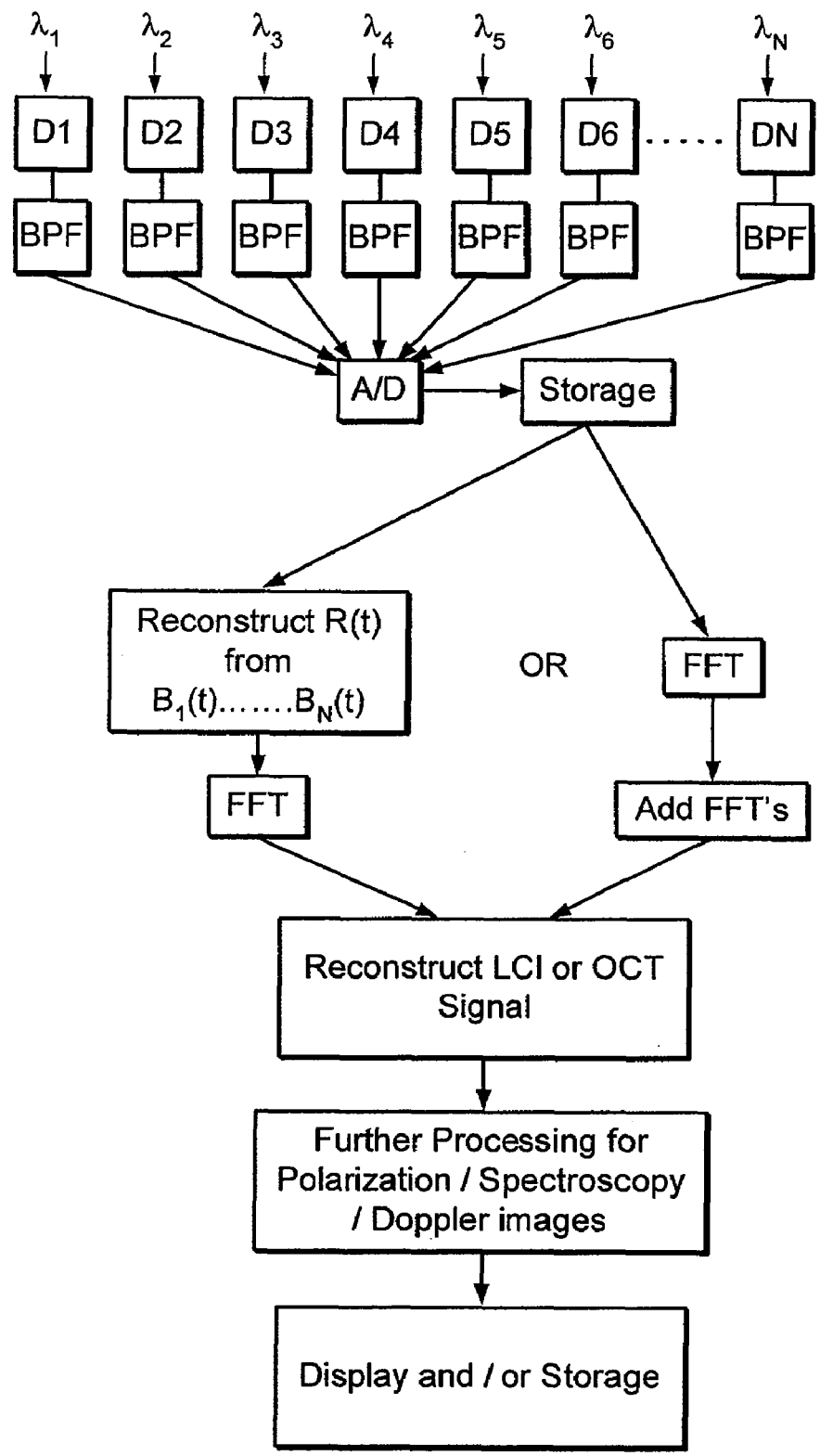
FIG. 11 is a flowchart depicting the reconstruction of LCI or OCT signal from wavelength bands.
Figure 12:
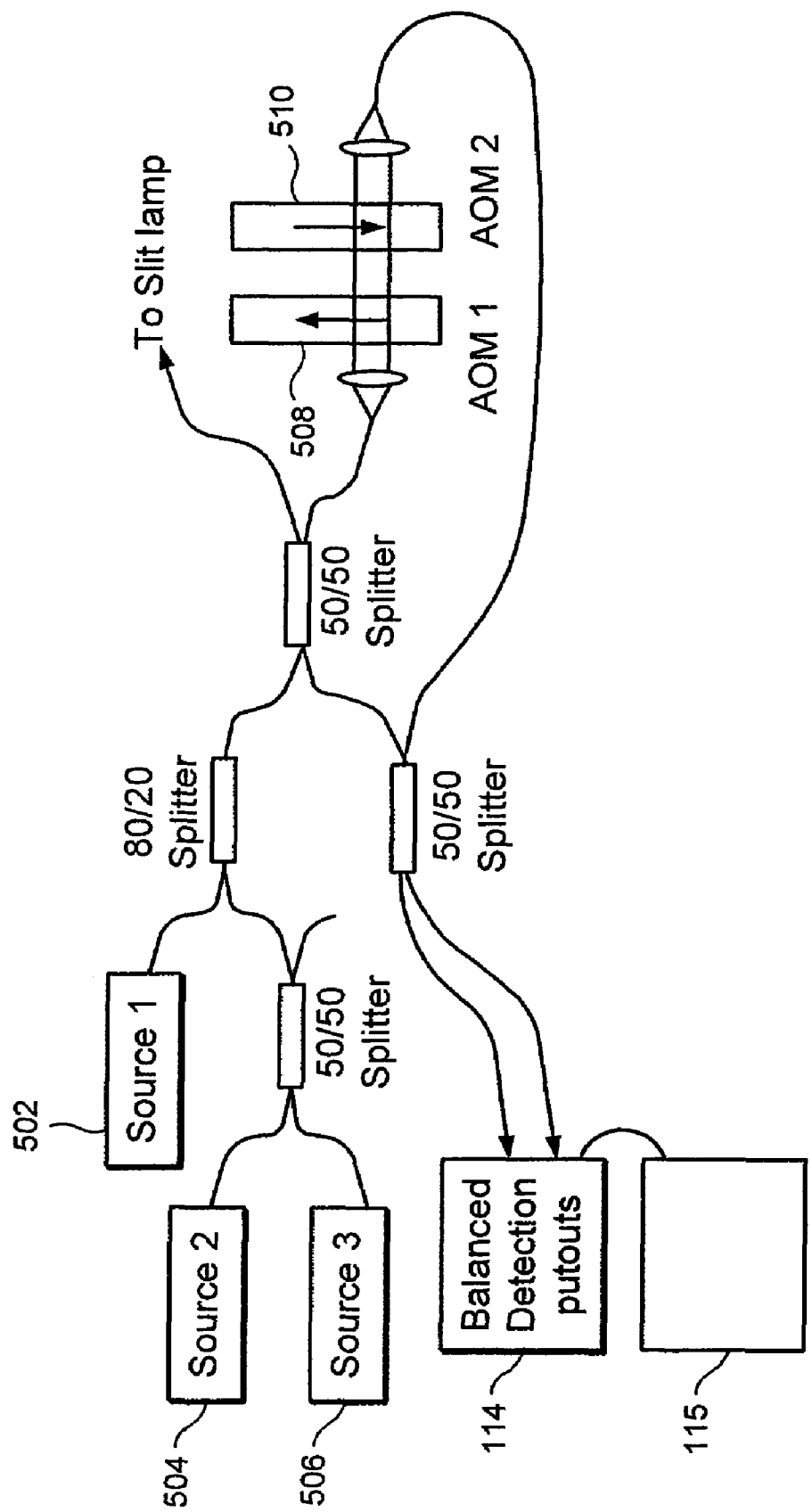
FIG. 12 is a schematic view of a spectral domain OCT interferometer design with a source combining the spectra of several superluminescent sources.
Figure 13:
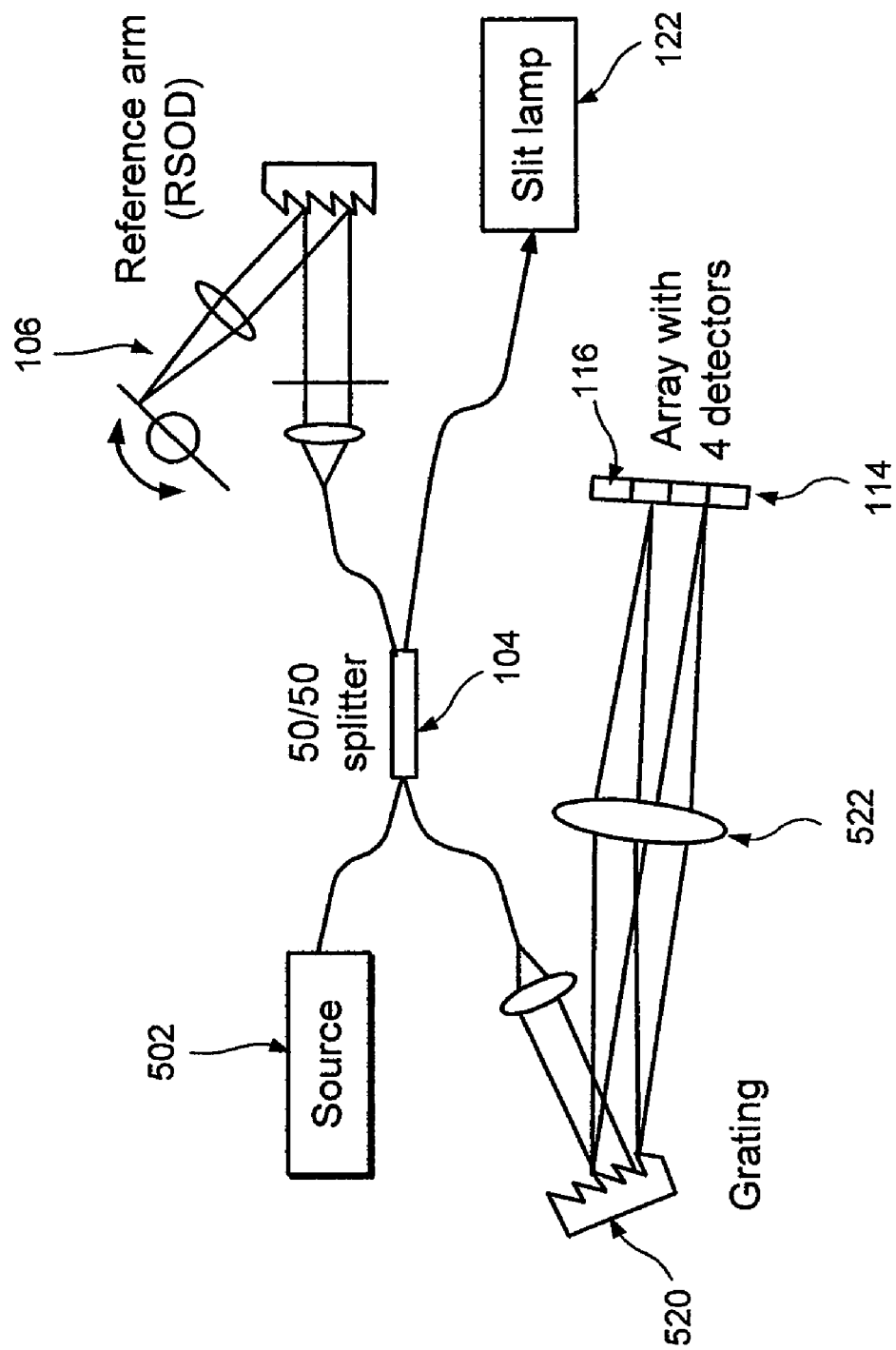
FIG. 13 is a schematic view of a system with a four detector array.
Figure 15:
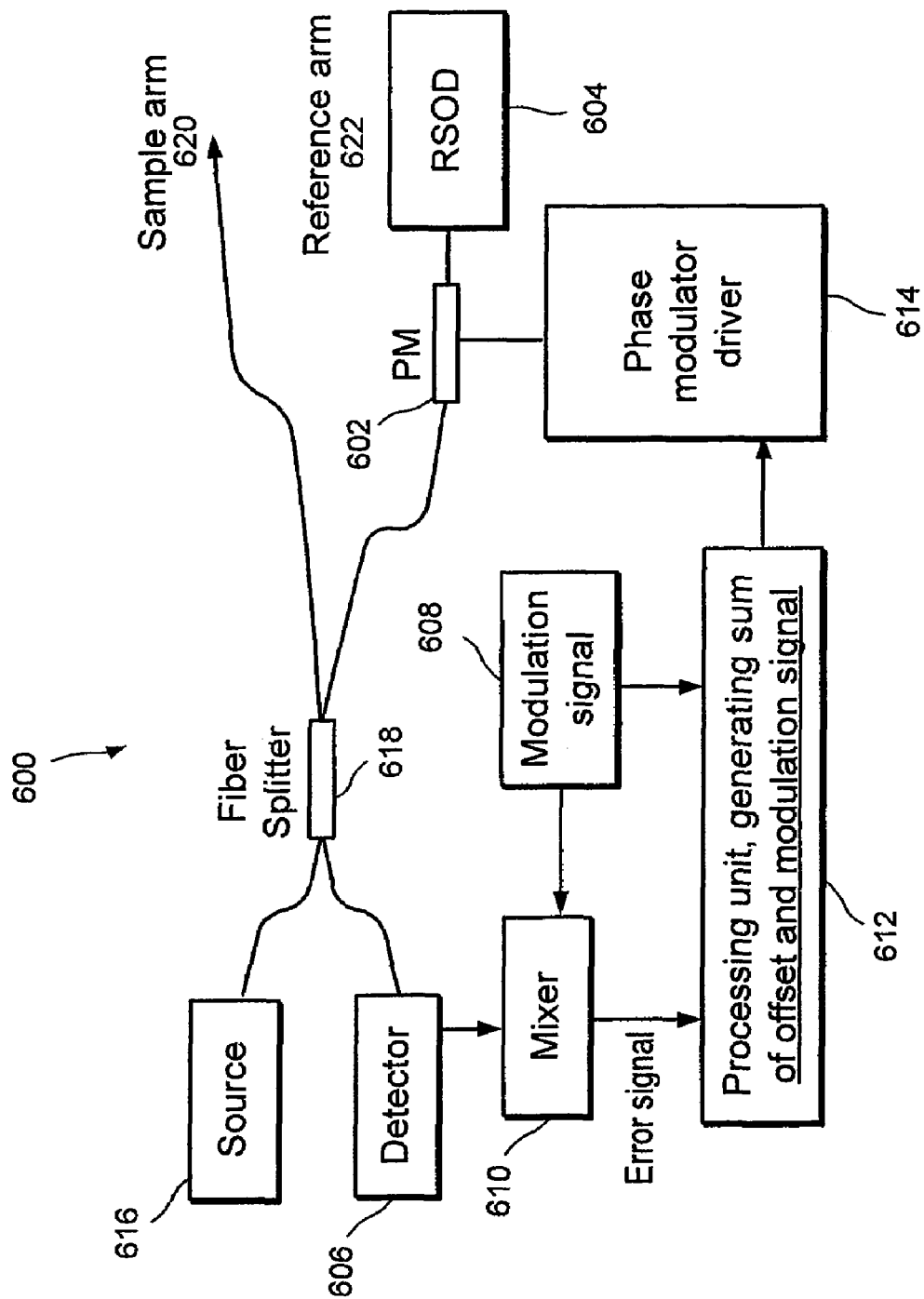
FIG. 15 is an embodiment of a phase tracker system with an extended phase lock range.
Figure 15A:
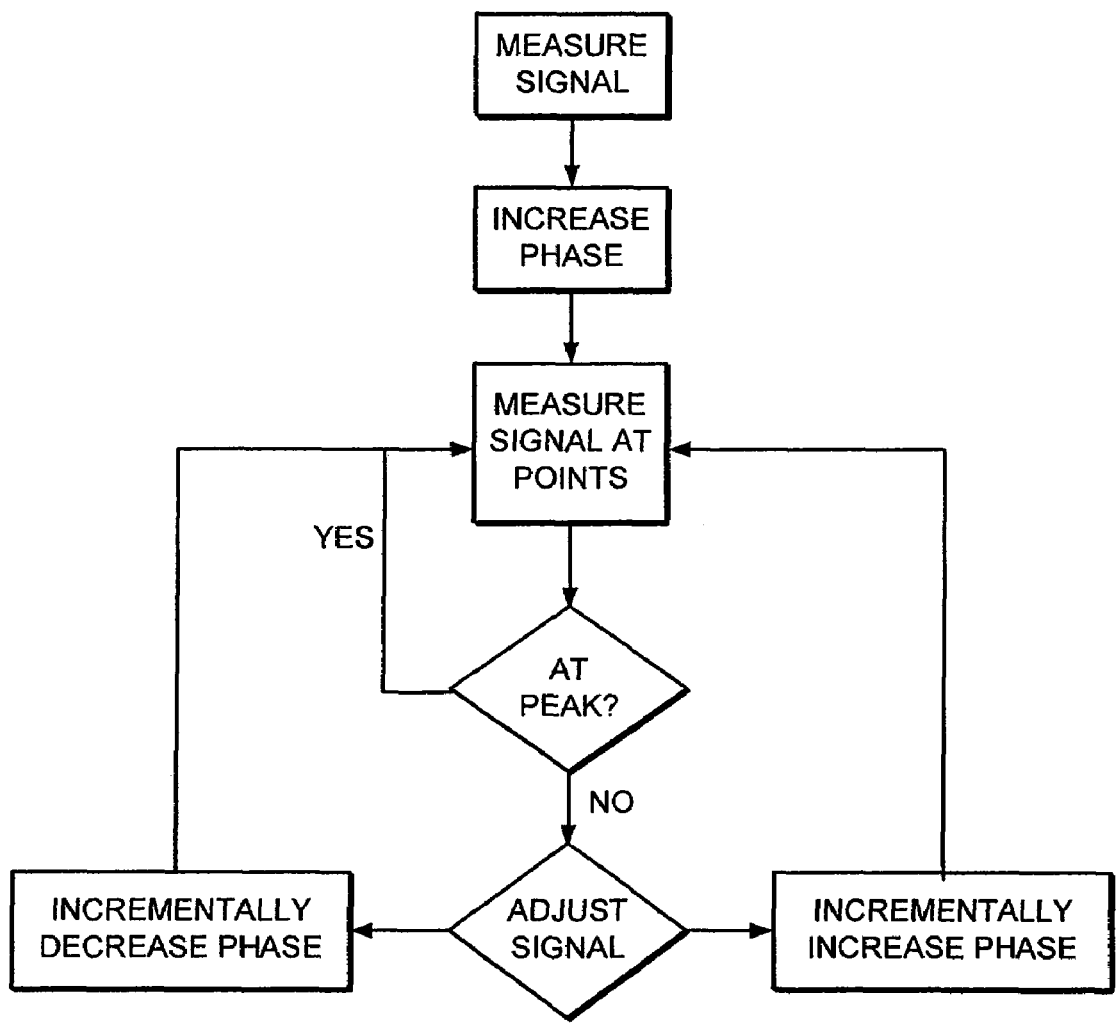
FIGS. 15A-C are flow diagrams of a method.
Figures 15B, 15C:
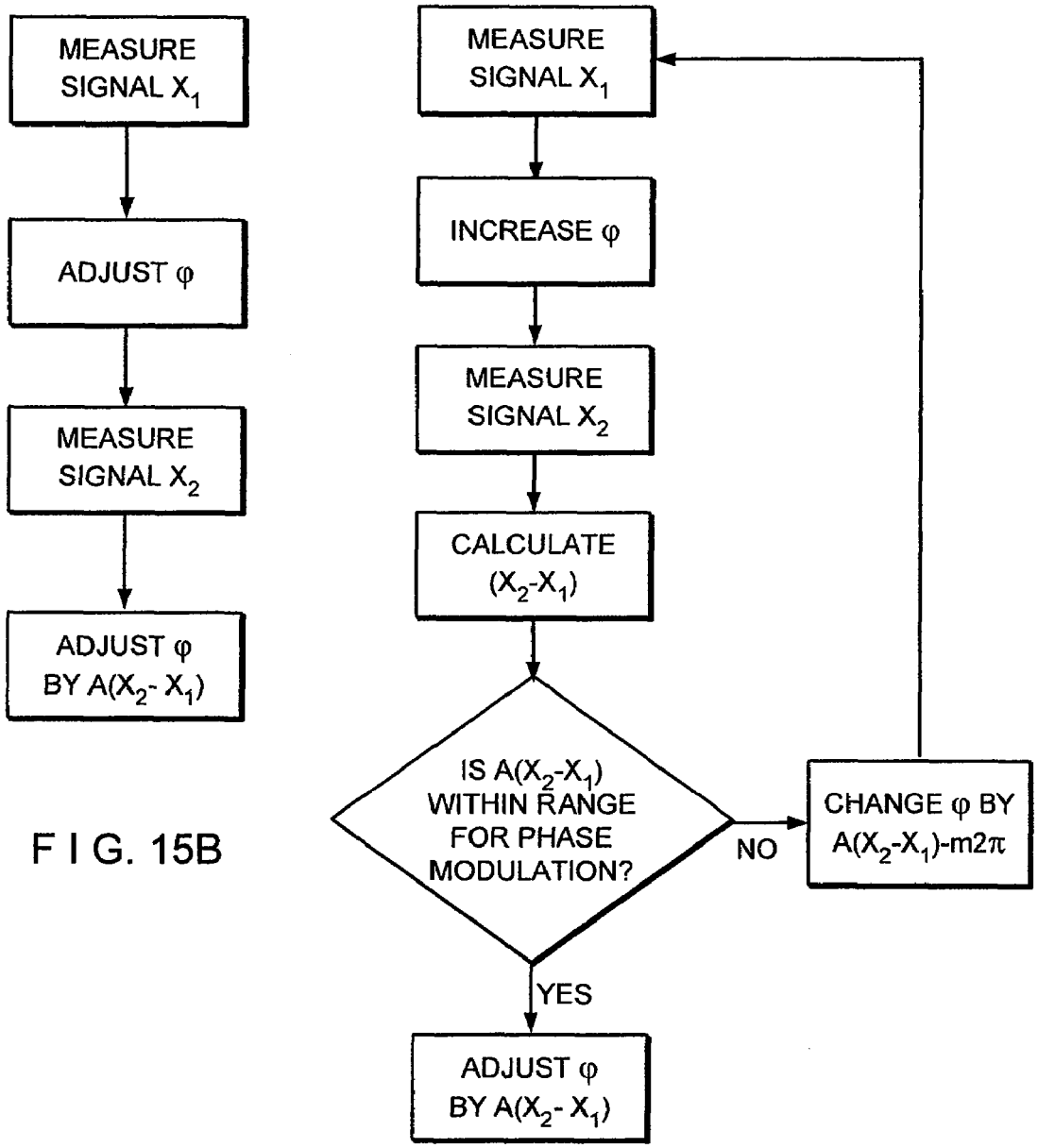
Figure 16:
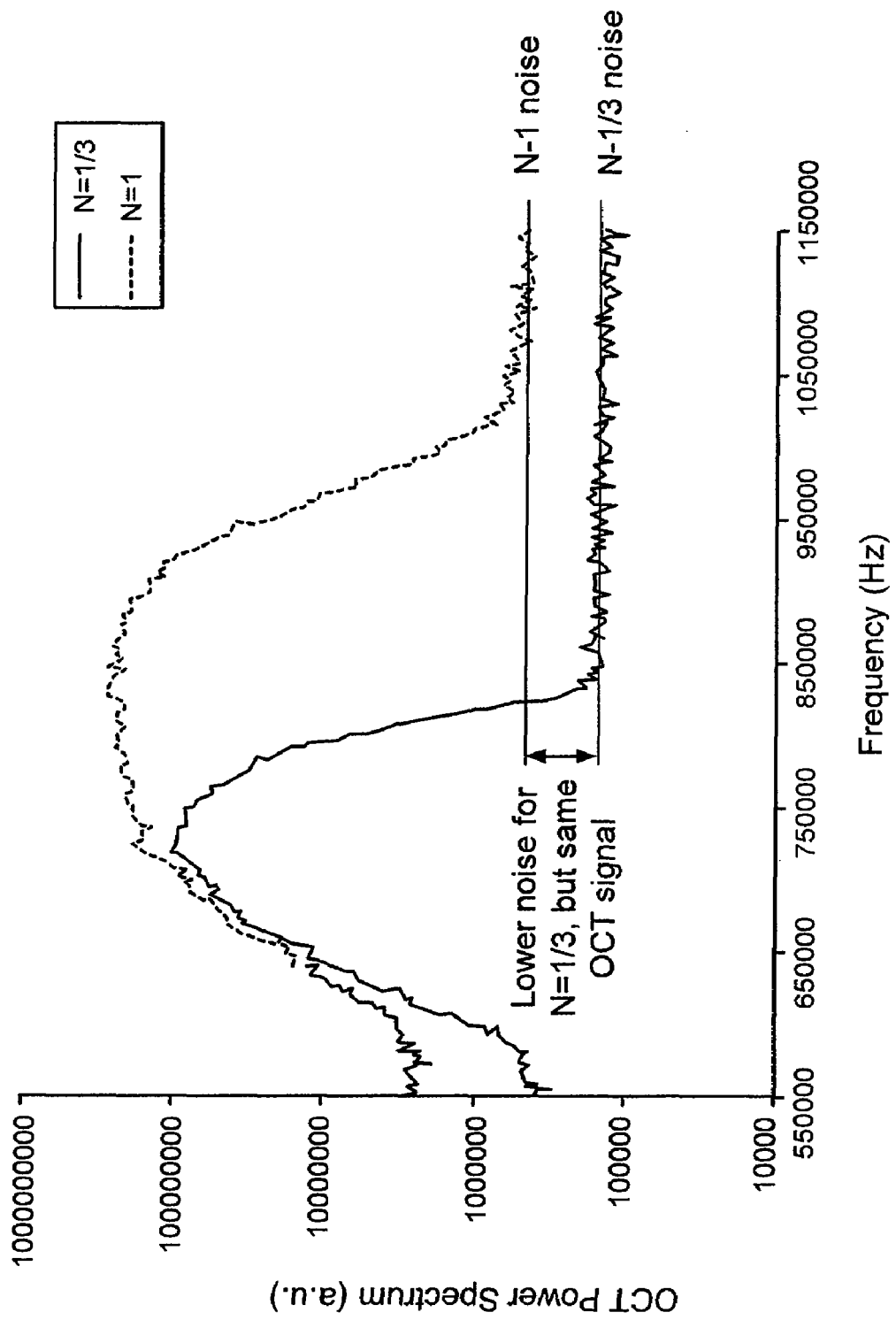
FIG. 16 is a graph of frequency versus OCT power spectrum.

Alternatively, another means for detection includes an integrating one-dimensional or two-dimensional CCD array which is capable of obtaining images at a rate greater than 1/f noise (approximately 10 kHz) (see FIG. 8). In this case the TIA is not needed and the BPF can be implemented discretely following digitization. An additional modification to this method includes using a second CCD for balanced detection which allows increased reference arm power and acquisition speed due to reduction of RIN. This method could be implemented using a single CCD with dual-balanced detection enabled by either interleaving dual balanced rows of the array detector or by placing two similar CCD detectors adjacent to one another.

Processing

The signal of each detector is band pass filtered around the signal frequency, such as by FFT's. The signal of all detectors can be combined as explained hereinabove to obtain the complex cross spectral density in the frequency domain. By Fourier transform, the complex cross spectral density can be converted to a depth profile in the tissue. Several methods to process the complex cross spectral density to obtain depth profile information are included by reference.

System Integration

Processing of the multiple signals may be performed using an imaging or diagnostic console which performs basic operations including, mathematical image reconstruction, display, data storage. Alternatively, another embodiment, shown in FIG. 2, envisions a standalone detection and processing system that may be connected to OCT and/or LCI systems already in use. In this case, the detector and digitization may be performed in the standalone unit. The input to the standalone unit would be the light combined from both reference and sample arms. The output of the system would be an interferometric signal similar to previous OCT or LCI console inputs, but with increased SNR. The standalone unit would contain the means for splitting the wavelengths into spectral bands, multiple detectors, analog electronics, including TIA's and means for reconstructing the interferometric signal. The means for reconstructing the interferometric signal would include either analog or digital means where the analog means includes band pass filters ("BPF's"), and analog means for adding the individual interferograms from each wavelength band. Digital means would include an analog to digital converter, CPU capable of recombining the interferograms from each spectral band into a single full bandwidth interferometric signal. The reconstructed interferogram may be then the output of the standalone system or alternatively, the reconstructed interferograms demodulated signal may be used as the input to the pre-existing system console.

Scan Range of the Reference Arm

The ranging depth in the sample is determined by the resolution with which the cross spectral density can be determined. In a method using a single detector the spectral resolution of the complex spectral density is determined by the scan range of the reference arm. The larger the scan range, the higher the spectral resolution and the larger the ranging depth in the sample. In a system with a spectral demultiplexing unit and multiple detectors, the resolution of the cross spectral density is a combination of reference arm scan range and spectral demultiplexing characteristics.

Any suitable wavelength band shape may be used for demultiplexing. For arbitrary spectral band shapes, the scan range of the reference arm is determined by the maximum path length delay that is needed to completely resolve the spectral components in each band. In cases where the wavelength band is determined by successive non-overlapping optical bandpass filters, a full scan length is needed and the SNR improvement is achieved by decreasing the width of the BPF for each spectral bands.

For instance, in one preferred embodiment, as depicted in FIG. 3, the spectral demultiplexing unit can split the spectrum into two bands where each band consists of a set of narrow spectra in a comb-like structure. Interleaving the comb-like spectral bands of each detector gives back a continuous spectrum. The resolution needed to resolve the spectrum at an individual detector is half of what it would need to be in a single detector system, and thus the scan range of the reference arm can be reduced by a factor of two, while maintaining the same ranging depth in the sample. In an alternative embodiment, the spectral demultiplexing unit can be in the reference arm. In FIG. 4 an example is shown for splitting up the spectrum in four spectral bands. In this example the scan range of the reference arm can be reduced by a factor of four while maintaining the same ranging depth in the sample.

Embodiments of the Demultiplexing Filter

Several techniques are known to demultiplex or disperse the spectrum. One method would use a grating and a micro lens array to focus spectral components onto individual detectors. A second method would use prisms instead of a grating. A third method would use a grating and an addressable mirror array (such as, but not limited to, a "MEMS" mirror or digital light processing "DLP" apparatus or the like) to direct spectral components to individual detectors. A fourth method would use a linear array of optical filters prior to the array of individual detectors. A fifth method would use waveguides etched into a material or manufactured from fiber optic components to generate a pattern with the desired filter action. As an example, in FIG. 4 an embodiment of a wave guide filter is drawn that will split the spectrum into bands. A sixth method would use arrayed waveguide gratings ("AWG") to create the interleaved or arbitrary spectral bands.

Relative Intensity Noise

One of the noise terms that are present at the detectors is relative intensity noise ("RIN") or Bose-Einstein noise. For a system where the sample arm optical power is negligible compared to the reference arm optical power at the detectors, RIN will become dominant for spectral widths less than a few nanometers at trans impedance amplifier bandwidths of 1 MHz. For many detector configurations, the spectral width at each detector will be smaller than a few nanometers, and the relative intensity noise will dominate the overall system noise. Thus, balanced detection needs to be implemented to eliminate the RIN. Several methods known in the art exist to implement balanced detection. One method will be discussed in more detail. Light from the reference arm and sample arm is incident on a grating at slightly different angles and reflected and focused onto a linear N×M photo detector array. Along the N direction (column) of the array, wavelength is encoded. Along the M direction (row) of the array, the interference pattern of the sample and reference arm at a particular wavelength is recorded. Since sample and reference arm light were incident at slightly different angles, a pattern of interference maxima and minima will be present in the column direction. Balanced detection can be implemented by subtracting diode signals that are exactly out of phase with respect to the maxima and minima pattern. Alternatively, balanced detection can be implemented by measuring the amplitude of the interference pattern in the column direction which may be accomplished by subtracting the maxima or the interference pattern from the minima of the interference pattern along the column.

Signal Processing to Reconstruct the Signal after Spectral Demultiplexing and Detection Two cases will be discussed as nonlimiting illustrations of the present invention, firstly the case of continuous spectral bands (blocks), and secondly the comb-like spectral bands as depicted in FIGS. 2 and 3.

Case A: Continuous spectral bands.

The detection arm light is split into N spectral blocks, where each spectral block contains the intensity between two optical frequencies, $$B_N = \int_{\omega_N}^{\omega_{N+1}} S_{ref}(\omega c/2v) d\omega$$

The signal for the full spectral width is obtained by an FFT of the signal in each band, an optional compensation of dispersion and other corrections to the phase and amplitude of each Fourier component to optimize the signal and to correct the spectral density for side lobe reduction, addition of the complex FFT spectra, and inverse FFT on the added complex FFT spectrum, optionally with data reduction before the inverse FFT, to obtain the optionally demodulated function R(t), which is the interferometric response for a depth scan with the full source spectrum.

Case B: Comb like spectral bands and the reconstruction of the full depth range in the sample arm from reduced reference arm scans.

The following discussion describes the principle of reconstruction of the full depth range in the sample arm from reduced reference arm scans. The procedure will be explained in the case of demultiplexing the spectrum in two spectral bands. The method can be expanded for demultiplexing into many spectral bands.

The signal at the detector for a single detector system is given by R(t). The depth range in the sample is given by the measurement time T of a single A-line (depth profile) times the group velocity generated by the reference arm delay line, $$z_{range} = v_g T$$

The smallest resolvable frequency after an FFT is given by 1/T, which gives a smallest resolvable angular frequency $\Delta\omega = 2\pi/T$. The filter as depicted in FIG. 4 splits the signal into two bands with peaks at $\omega = \omega_0, \omega_0 + 2\Delta\omega, \omega_0 + 4\Delta\omega$, etc. and $\omega = \omega_0 + \Delta\omega, \omega_0 + 3\Delta\omega$, etc., respectively.

$B_1(t)$ and $B_2(t)$ are the signals in band one and two respectively. The signal in spectral bands one and two after Fourier transform are given by $B_1(\omega) = R(\omega)\cos^2(\omega T/4)$ and $B_2(\omega) = R(\omega)\sin^2(\omega T/4)$.

This product in the Fourier domain can also be written as a convolution in the time domain. Assuming the signals periodic with time T, the signals $B_1(t)$ and $B_2(t)$ are given by $B_1(t) = R(t) + R(t+T/2)$ and $B_2(t) = R(t) - R(t+T/2)$.

Using the above equations, the signal R(t) from t=0 to t=T can be reconstructed from the signals $B_1(t)$ and $B_2(t)$ recorded from t=0 to t=T/2 by writing, $R(t) = B_1(t) + B_2(t)$ and $R(t+T/2) = B_1(t) - B_2(t)$ for $0 < t < T/2$. For higher N>2, the identical procedure is performed such that R(t) is reconstructed from $B_1$ to $B_N$.

This demonstrates that the signals $B_1(t)$ and $B_2(t)$ only need to be recorded over half the depth range $z_{range}$. Thus, the depth ranging in the reference arm can be reduced by a factor of 2 while the ranging depth in the sample remains the same. If the signal is split into more spectral bands, like shown in FIG. 3, a similar procedure as described above allows reduction of the depth scan in the reference arm by a factor of N, while the ranging depth in the sample remains the same, and N the number of spectral bands.

Figure 7:
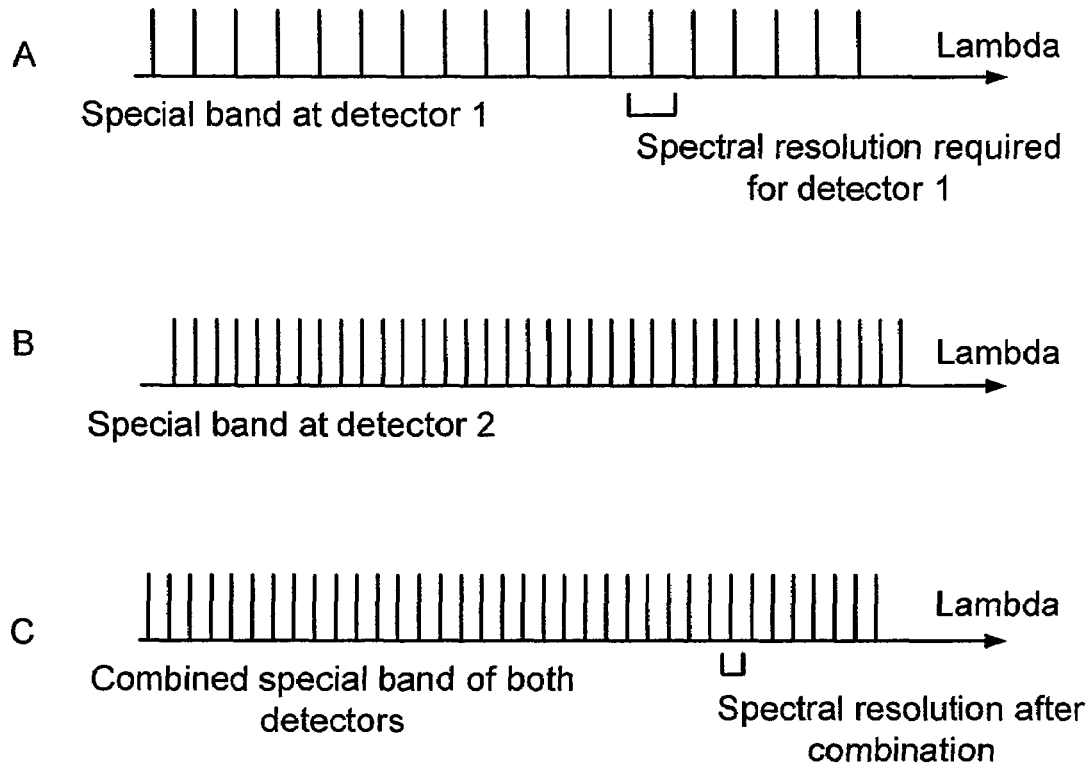
FIG. 7 is a flowchart depicting the reconstruction of LCI or OCT signal from wavelength bands.

A flow diagram of the procedure described above is given in FIG. 7.

Case B2. Limit of Large Number of Spectral Bands

In the limit of a large number of spectral bands, $$N \geq \frac{L}{\lambda},$$

the optical path length change in the reference arm approaches that of a wavelength, λ. In this limit, only a phase change across one wavelength is needed for reconstructing the entire axial scan over length L. In this case, the reference arm path delay may be accomplished by using any of the aforementioned means for scanning the reference arm delay. Other preferred methods include insertion of an electrooptic modulator, acoustooptic modulator or phase control rapidly scanning optical delay line ("RSOD") in the reference arm path to impart the path length delay of one wavelength. Also in this case, the wavelength demultiplexing unit does not separate the wavelengths into a comb pattern, but demultiplexes the spectrum into unique optical frequencies, with each frequency detected by a single detector.

Case C. Fourier Domain Reconstruction for Arbitrary Wavelength Patterns

As opposed to reconstruction of the LCI or OCT signal in the time or space domains, the signal may be reconstructed in the Fourier domain by adding the complex spectral components for each wavelength band to compose the Fourier transform of the LCI or OCT signal. Alterations of the phase for each Fourier component may be needed in some circumstances to correct for minimization of reference arm delay length.

Reconstruction of the Image or One Dimensional Axial Scan

Following reconstruction of the LCI or OCT signal in the real domain, the axial reflectivity may be determined by demodulating the reconstructed LCI or OCT signal. Means for demodulation include, multiplication by a sinusoid and low pass filtering, envelope demodulation using envelope detection, square law demodulation and low pass filtering, quadrature demodulation followed by FIR, IIR filtering, or low pass filtering. In addition, known to those skilled in the art, is reconstruction of Stokes vectors (polarization) and flow from these LCI or OCT signals. Following reconstruction and demodulation, the data may be displayed in one or two-dimensional format (image) for interpretation and ultimately diagnosis of a tissue condition or defect in a medium. If one reconstructs the LCI or OCT signal in the Fourier domain, the reconstructed signal in the Fourier domain can be demodulated in the Fourier domain by shifting the Fourier spectrum and performing an inverse Fourier transform. As a result, the complex signal in the real domain (quadrature signal) is then reconstructed into axial reflectivity information by computing the amplitude of the real portion of the quadrature signal. The complex component is used for computing polarization or flow information. Alternatively, if the signal is reconstructed in the Fourier domain, it can be directly inverse Fourier transformed into the real domain and undergo the aforementioned processing described for the reconstructed real domain signals.

ADVANTAGES

The present invention reduces shot noise which allows for much lower source powers, or much higher acquisition rates than current systems. The increased detection sensitivity allows for real time imaging. Such imaging speed can help practitioners where motion artifacts are a continuing problem, such as in gastrointestinal, ophthalmic and arterial imaging environments. By increasing the frame rate while maintaining or improving the signal to noise ratio such artifacts can be minimized.

The invention will be further described in connection with the following examples, which are set forth for purposes of illustration only.

EXAMPLE

The method was verified in the lab by the following experiment.

Figure 5:
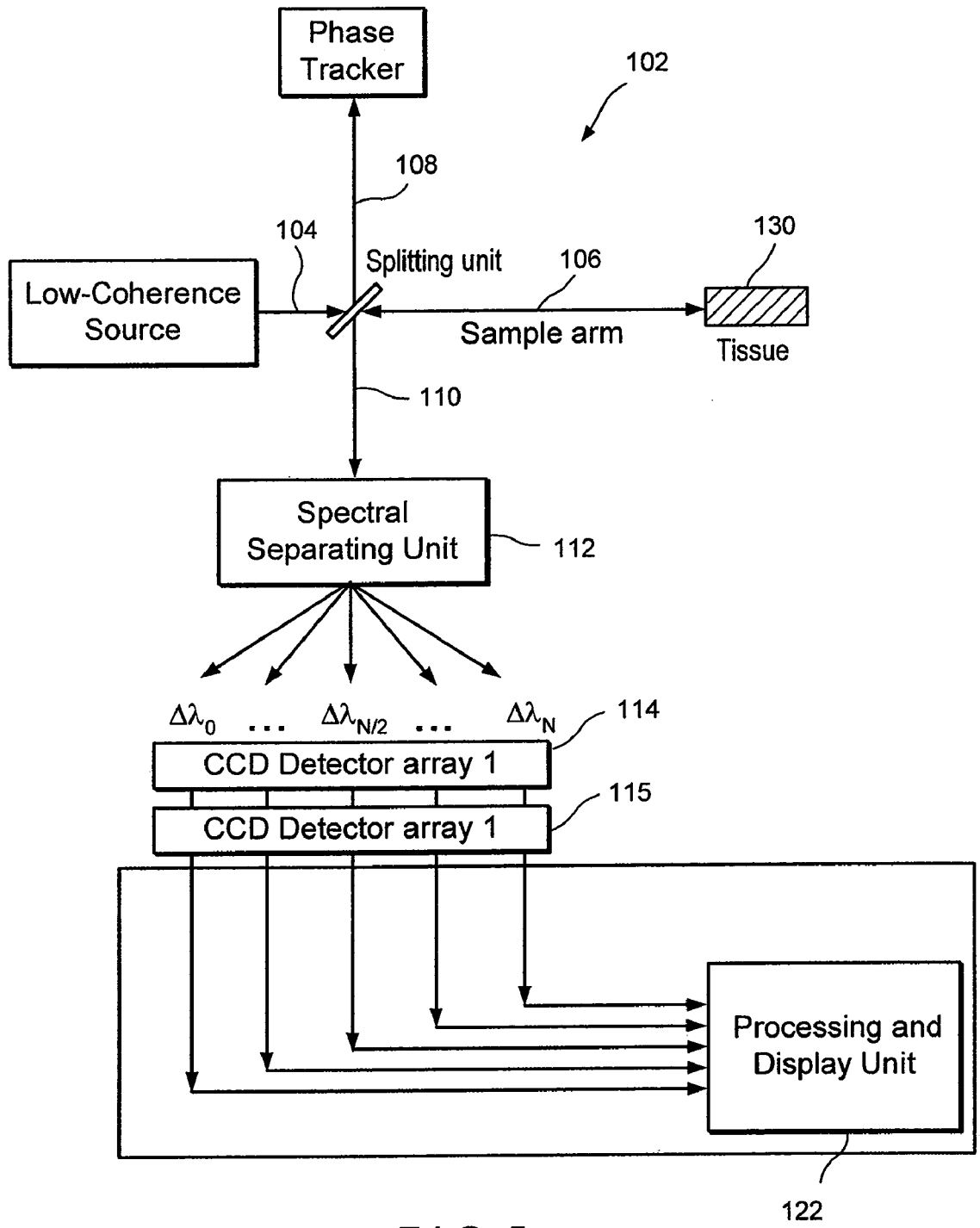
FIG. 5 is a graph of frequency versus OCT power spectrum.

In the existing OCT system, the shot noise power spectrum as determined from the spectral density due to the reference arm optical power was measured. Then ⅔ of the spectrum from the reference arm was blocked, and experimentally it was verified that the shot noise power spectrum was reduced by a factor of three, thus demonstrating that the shot noise is reduced by a factor of 3 if the spectrum is split in three spectral bands (see FIG. 5). The upper curve (gray dotted line) shows the power spectrum for the OCT signal with one detector. For the lower curve (solid line), the spectrum was limited by ⅓ with a corresponding factor of 3 improvement in signal to noise ratio. This data was generated by experiment, blocking ⅔ of the spectrum in a grating-based double-passed pulse shaping rapidly scanning optical delay line.

Figure 6:
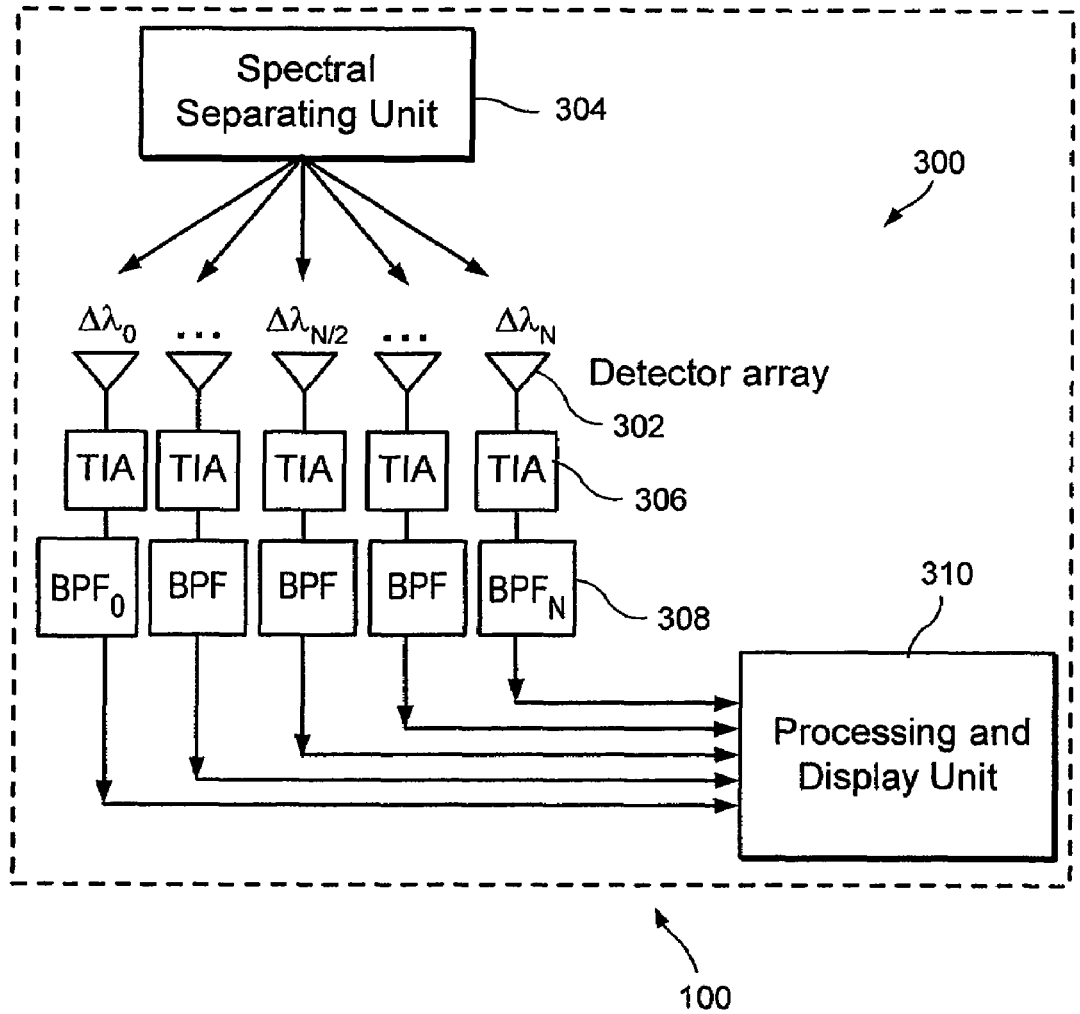
FIG. 6 is a graph of frequency versus amplitude spectrum subtracted from the shot noise (experimental data) for the N=1 (dotted line) and N=⅓ (solid line) cases.

An object with low reflectivity was inserted in the sample arm. Using the full spectral width of the source, the power spectrum of the interference between sample and reference arm light was determined in the lower half of the spectral density. Then the upper part of the source spectrum was blocked in the reference arm, and it was verified that the lower ⅓ of the power spectrum of the interference between sample and reference arm light had the same magnitude as in the previous measurement (see FIG. 6). This figure demonstrates that the signal amplitude is equal for the N=1 and N=⅓ cases where they overlap. The result of equal amplitude signal for N=⅓ case and the 3-fold lower noise for the N=⅓ case (see FIG. 2) demonstrates that splitting into N wavelength bands increases the SNR by a factor of N.

This demonstrates that when the light in the detection arm is split in two spectral bands, the spectral density of the interference between sample and reference arm light within the spectral bandwidth of a single detector is unchanged. Combined with the measurement that showed a reduction in the shot noise power spectrum, the conclusion is that a reduction of shot noise can be realized by splitting the detection arm light in separate spectral bands.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. It should further be noted that any patents, applications and publications referred to herein are incorporated by reference in their entirety.

What is claimed is:

1. An apparatus for optical imaging, comprising:
   a) an interferometer configured to receive at least one electro-magnetic radiation from a transmissive reference, and generate the at least one signal at least one signal as a function of the at least one electro-magnetic radiation;
   b) a spectral separating unit which splits the at least one signal received from the interferometer into a plurality of optical frequencies; and
   c) a plurality of detectors, each detector being configured to detect at least a portion of the optical frequencies received from the spectral separating unit, wherein the spectral separating unit comprises at least one of (i) an addressable mirror array or (ii) a waveguide filter.

2. The apparatus according to claim 1, wherein the spectral separating unit splits the signal into the bands.

3. The apparatus according to claim 1, wherein the detectors are provided in a form of a two-dimensional array.

4. The apparatus according to claim 1, wherein a sample is scanned in a series of simultaneous illuminations of substantially all of areas of the sample to provide at least one radiation associated with the sample to be used by the interferometer to provide the at least one signal.

5. The apparatus according to claim 1, wherein the interferometer comprises an arrangement generating a path length difference that is a fraction of a ranging depth of the interferometer.

6. An apparatus for optical imaging, comprising:
   a) an interferometer structured to provide at least one signal;
   b) a spectral separating unit which splits the at least one signal received from the interferometer into a plurality of optical freguencies; and
   c) a plurality of detectors, each detector being configured to detect at least a portion of the optical freguencies received from the spectral separating unit, wherein the spectral separating unit comprises at least one of (i) an addressable mirror array or (ii) a waveguide filter, wherein the spectral separating unit comprises a polarization separating unit.

7. An apparatus for optical imaging, comprising:
a) an interferometer structured to provide at least one signal;
b) a spectral separating unit which splits the at least one signal received from the interferometer into a plurality of optical frequencies;
c) a plurality of detectors, each detector being configured to detect at least a portion of the optical frequencies received from the spectral separating unit, wherein the spectral separating unit comprises at least one of (i) an addressable mirror array or (ii) a waveguide filter; and
d) an arrangement which configured to at least one of:
  i. reconstruct the signal from the detectors by a mathematical manipulation of each plurality of signals obtained from the detectors, or
  ii. track a phase of the signal of the interferometer.

8. An apparatus for optical imaging, comprising:
a) an interferometer structured to provide at least one signal;
b) a spectral separating unit which splits the at least one signal received from the interferometer into a plurality of optical frequencies; and
c) a plurality of detectors, each detector being configured to detect at least a portion of the optical frequencies received from the spectral separating unit, wherein the spectral separating unit comprises at least one of (i) an addressable mirror array or (ii) a waveguide filter, wherein the spectral separating unit splits the signal into a plurality of bands, whereby at least one of the bands comprises spectra that has a comb-like structure.

9. An apparatus for optical imaging, comprising:
a) an interferometer structured to provide at least one signal;
b) a spectral separating unit which splits the at least one signal received from the interferometer into a plurality of optical frequencies;
c) a plurality of detectors, each detector being configured to detect at least a portion of the optical frequencies received from the spectral separating unit, wherein the spectral separating unit comprises at least one of (i) an addressable mirror array or (ii) a waveguide filter; and
d) an arrangement which configured to track a phase of the at least one signal of the interferometer.

10. An apparatus for optical imaging, comprising:
a) an interferometer structured to receive at least one electro-magnetic radiation from a reference and provide at least one signal;
b) a spectral separating unit which splits the at least one signal received from the interferometer into a plurality of optical frequencies; and
c) a plurality of detectors, each detector being configured to detect at least a portion of the optical frequencies received from the spectral separating unit, wherein the spectral separating unit comprises at least one of (i) an addressable mirror array or (ii) a waveguide filter.

* * * * *